(12) United States Patent
Blissard et al.

(10) Patent No.: US 7,405,038 B1
(45) Date of Patent: Jul. 29, 2008

(54) STABLE CELL LINES RESISTANT TO APOPTOSIS AND NUTRIENT STRESS AND METHODS OF MAKING SAME

(75) Inventors: Gary Blissard, Ithaca, NY (US); Robert R. Granados, Ithaca, NY (US); Guangyun Lin, Ithaca, NY (US)

(73) Assignee: Boyce Thompson Institute for Plant Research, Inc., Ithaca, NY (US)

( * ) Notice: Subject to any disclaimer, the term of this patent is extended or adjusted under 35 U.S.C. 154(b) by 0 days.

(21) Appl. No.: 09/518,763

(22) Filed: Mar. 3, 2000

(51) Int. Cl.
C12N 15/63 (2006.01)
C12N 15/64 (2006.01)
C12N 15/866 (2006.01)
C12N 5/10 (2006.01)
C12Q 1/68 (2006.01)
C12Q 1/70 (2006.01)
C12P 21/00 (2006.01)
C07K 7/00 (2006.01)

(52) U.S. Cl. .......................... 435/5; 435/6; 435/320.1; 435/69.1; 435/325; 435/348; 435/455; 435/456

(58) Field of Classification Search ................ 435/69.1, 435/325, 348, 366, 320.1, 5, 6, 7.1, 91.4, 435/91.41
See application file for complete search history.

(56) References Cited

FOREIGN PATENT DOCUMENTS

| WO | WO 99/15677 | 4/1999 |
| WO | WO 01/23592 | 4/2001 |

OTHER PUBLICATIONS

Granados, R.R. and Hashimoto, Yoshifumi, Chapter 1: Infectivity of Baculoviruses to Cultured Cells, pp. 3-13. in Invertebrate Cell System Applications, vol. II, Jun Mitsuhashi, Editor, CRC Press, Florida, 1989.

Ayres, M.D., Howard,S.C., Kuzio,J., Lopez-Ferber,M. and Possee,R. D. The complete DNA sequence of Autographa californica nuclear polyhedrosis virus. *Virology* 202 (2), 586-605 (1994).

Beidler, D. R., Tewari, M., Friesen, P. D., Poirier, G. & Dixit,, V. M. The Baculovirus p35 protein inhibits Fas- and tumor necrosis factor-induced apoptosis. *J Biol Chem* 270, 16526-16528 (1995).

Bertin, J. et al. Apoptotic suppression by baculovirus P35 involves cleavage by and inhibition of a virus-induced CED-3-ICE-like protease. *Journal of Virology*. 70, 6251-6259 (1996).

Blissard, G. W. & Rohrmann, G. F. Baculovirus gp64 gene expression: Analysis of sequences modulating early transcription and transactivation by IE1. *J. Virol.* 65, 5820-5827 (1991).

Bump, N. J. et al. Inhibition of ICE family proteases by baculovirus antiapoptotic protein *p35*. *Science* 269, 1885-1888 (1995).

Cartier, J. L., Hershberger, P. A. & Friesen, P. D. Suppression of apoptosis in insect cells stably transfected with baculovirus p35: Dominant interference by N terminal sequences p35l-76. *Virology* 68, 7728-7737 (1994).

Chang, M.-J., Kuzio, J. & Blissard, G. W. Modulation of translational efficiency by contextual nucleotides flanking a baculovirus initiator AUG codon. *Virology* 259, 369-383 (1999).

Clem, R. J., Fechheimer, M. & Miller, L. K. Prevention of apoptosis by a baculovirus gene during infection of insect cells. *Science* 254,1388-1390 (1991).

Cryns, V. & Yuan, J. Proteases to die for [published erratum appears in Genes Dev Feb. 1, 1999;13(3):371]. *Genes Dev* 12, 1551-1570 (1998).

Davis, T. R. et al. Comparative recombinant protein production in eight insect cell lines. In Vitro *Cell Dev Biol* 29A, 388-390 (1993).

Davis, T. R., Trotter, K. M., Granados, R. R. & Wood, H. A. Baculovirus expression of alkaline phosphatase as a reporter gene for evaluation of production, glycosylation and secretion. *Biotechnology (N Y)* 10, 1148-1150 (1992).

Fisher, A. J., Cruz, W., Zoog, S. J., Schneider, C. L. & Friesen, P. D. Crystal structure of baculovirus P35: role of a novel reactive site loop in apoptotic caspase inhibition. *EmboJ 18*, 2031-2039 (1999).

Gage, L. P. The Bombyx mori genome: analysis by DNA reassociation kinetics. *Chromosoma* 45, 27-42 (1974).

Hay, B. A., Wolff, T. & Rubin, G. M. Expression of baculovirus P35 prevents cell death in Drosophila. *Development 120*, 2121-2129 (1994).

Hershberger, P. A., Lacount, D. J. & Friesen, P. D. The apoptotic suppressor P35 is required early during baculovirus replication and is targeted to the cytosol of infected cells. *Jotirnal of Virology 68*, 3467-3477 (1994).

Martin, S. J. & Green, D. R. Protease activation during apoptosis: death by a thousand cuts? *Cell 82*, 349-352 (1995).

Martinou, I. et al. Viral Proteins ElB19K and p35 Protect Sympathetic Neurons from Cell Death Induced by NGF Deprivation. *Journal of Cell Biology*. 128, 201-208 (1995).

Milner, A.E., Johnson, G.D., and Gregory, C.D. Prevention of Programmed Cell Death in Burkitt Lymphoma Cell Lines by bcl-2 Dependent and Independent Mechanisms. *International Journal of Cancer* 52: 636-644 (1992).

Monsma, S. A. & Blissard, G. W. Identification of a membrane fusion domain and an oligomerization domain in the baculovirus GP64 Envelope Fusion Protein. *J. Virol.* 69, 2583-2595 (1995).

Monsma, S. A., Oomens, A. G. P. & Blissard, G. W. The GP64 Envelope Fusion Protein is an essential baculovirus protein required for cell to cell transmission of infection. J. *Virol.* 70, 4607-4616 (1996).

(Continued)

Primary Examiner—David Guzo
(74) Attorney, Agent, or Firm—Brown & Michaels, PC

(57) ABSTRACT

Cell lines that are commonly used for protein expression are engineered to include genes that encode suppressors of apoptosis (SA). Insect cell lines expressing these SA genes are resistant to apoptosis or programmed cell death, and express certain recombinant proteins at increased levels. These cell lines also have increased resistance to many types of stress. Because some of the SA proteins inhibit apoptosis in a wide spectrum of organisms, these genes may be inserted into other plant or animal cell lines for a variety of purposes involving resistance to apoptosis or resistance to stress.

7 Claims, 6 Drawing Sheets

OTHER PUBLICATIONS

Rabizadeh, S., Lacount, D. J., Friesen, P. D. & Bredesen, D. E. Expression of the baculovirus p35 gene inhibits -mammalian neural cell death. *Journal of Neurochemistry* 61. 2318-2321 (1993).

Rasch, E. M. The DNA content of sperm and hemocyte nuclei of the silkworm, Bombyx mori L. *Chromosoma* 45,1-26 (1974).

Robertson, N. M. et al. Baculovirus P35 inhibits the glucocorticoid -mediated pathway to cell death. *Cancer Research*. 57, 43-47 (1997).

Sugimoto, A., Friesen, P. D. & Rothman, J. H. Baculovirus p35 prevents developmentally programmed cell death and rescues a ced-9 mutant in the nematode Caenorhabditis elegans. *EMBO J*. 13, 2023-2028 (1994).

Wang, P., Granados, R. R. & Shuler, M. L. Studies on serum-free culture of insect cells for virus propagation and recombinant protein production. *J Invertebr Pathol* 59, 46-53 (1992).

Wickham, T. J. in *Department of Chemical Engineering* 208 (Cornell University, Ithaca, NY, 1991).

Wickham, T. J., Davis, T., Granados, R. R., Shuler, M. L. & Wood, H. A. Screening of insect cell lines for the production of recombinant proteins and infectious virus in the baculovirus expression system. *Biotechnol Prog* 8, 391-396 (1992).

Xue, D. & Horvitz, H. R. Inhibition of the Caenorhabditis elegans cell-death protease CED-3 by a CED-3 cleavage site in baculovirus p35 protein, *Nature* (London). 377, 248-251 (1995).

Yu, Z., Podgwaite, J. D. & Wood, H. A. Genetic engineering of a Lymantria dispar nuclear polyhedrosis virus for expression of foreign genes. *J. Gen Virol* 73, 1509-1514 (1992).

Clem, R. J. & Miller, L. K. Apoptosis reduces both the in-vitro replication and the in-vivo infectivity of a baculovirus. *J Virol* 67, 3730-3738 (1993).

Lee, J. C., Chen, H. H., Wei, H. L. & Chao, Y. C. Superinfection-Induced Apoptosis and Its Correlation with the Reduction of Viral Progeny in Cells Persistently Infected with Hz-1 Baculovirus. *J Virol* 67, 6989-6994 (1993).

Lerch, R. A. & Friesen, P. D. The 35-kilodalton protein gene p35 of autographa-californica nuclear polyhedrosis virus and the neomycin resistance gene provide dominant selection of recombinant baculoviruses. *Nucleic Acids Res* 21, 1753-1760 (1993).

Birnbaum, M. J., Clem, R. J. & Miller, L. K. An apoptosis-inhibiting gene from a nuclear polyhedrosis virus encoding a polypeptide with Cys-His sequence motifs. Journal of Virology 68, 2521-2528 (1994).

Gong, M. & Guarino, L. A. Expression of the 39k Promoter of Autographa californica Nuclear Polyhedrosis Virus Is Increased by the Apoptotic Suppressor P35. Virology 204, 38-44 (1994).

Ribeiro, B. M., Hutchinson, K. & Miller, L. K. A mutant baculovirus with a temperature-sensitive IE-1 transregulatory protein. J. Virol. 68, 1075-1084 (1994).

Clem, R. J. & Miller, L. K. Control of Programmed Cell Death by the Baculovirus Genes p35 and iap. Molecular and Cellular Biology 14, 5212-5222 (1994).

Clem, R. J. & Miller, L. K. in Communications in Cell & Molecular Biology, vol. 8. Apoptosis II: The molecular basis of apoptosis in disease. 89-110 (Cold Spring Harbor Laboratory Press, Plainview, New York, USA, 1994).

Crook, N. E., Clem, R. J. & Miller, L. K. An apoptosis-inhibiting baculovirus gene with a zinc finger-like motif. J Virol 67, 2168-2174 (1993).

Roy, N. et al. The gene for Neuronal Apoptosis Inhibitory Protein is partially deleted in individuals with spinal muscular atrophy. Cell 80, 167-178 (1995).

Clem, R. J., Robson, M. & Miller, L. K. Influence of infection route on the infectivity of baculovirus mutants lacking the apoptosis-inhibiting gene p35 and the adjacent gene p94. Journal of Virology. 68, 6759-6753 (1994).

Lu, A. & Miller, L. K. The roles of eighteen baculovirus late expression factor genes in transcription and DNA replication. J. Virol. 69, 975-982 (1995).

Todd, J. W., Passarelli, A. L. & Miller, L. K. Eighteen baculovirus genes, including lef-11, p35, 39K, and p47, support late gene expression. J. Virol. 69, 968-974 (1995).

Reed, J. C. Bcl-2 and the regulation of programmed cell death. Journal of Cell Biology. 124, 1-6 (1994).

Chejanovsky, N. & Gershburg, E. The wild-type Autographa californica nuclear polyhedrosis virus induces apoptosis of *Spodoptera littoralis* cells. Virology 209, 519-525 (1995).

Ahrens, C. H. & Rohrmann, G. F. Replication of Orgyia pseudotsugata baculovirus DNA: lef-2 and ie-1 are essential and ie-2, p34, and Op-iap are stimulatory genes. Virology. 212, 650-662 (1995).

Singh, R. P., Al Rubeai, M., Gregory, C. D. & Emery, A. N. Cell death in bioreactors: A role for apoptosis. Biotechnology and Bioengineering. 44, 720-726 (1994).

Singh, R. P., Emery, A. N. & Al-Rubeai, M. Enhancement of survivability of mammalian cells by overexpression of the apoptosis-suppressor gene bcl-2. Biotechnology and Bioengineering 52, 166-175 (1996).

Todd, J. W., Passarelli, A. L., Lu, A. & Miller, L. K. Factors regulating baculovirus late and very late gene expression in transient-expression assays. Journal of Virology. 70, 2307-2317 (1996).

Prikhod'ko, E. A. & Miller, L. K. Induction of apoptopsis by baculovirus transactivator IE1. Journal of Virology. 70, 7116-7124 (1996).

Palli, S. R. et al. CfMNPV blocks AcMNPV-induced apoptosis in a continuous midgut cell line. Virology. 222, 201-213 (1996).

Duckett, C. S. et al. A conserved family of cellular genes related to the baculovirus iap gene and encoding apoptosis inhibitors. Embo Journal. 15, 2685-2694 (1996).

White, K., Tahaoglu, E. & Steller, H. Cell killing by the Drosophila gene reaper. Science (Washington D C). 271, 805-807 (1996).

Liston, P. et al. Suppression of apoptosis in mammalian cells by NAIP and related family of IAP genes. Nature (London). 379, 349-353 (1996).

Hay, B. A., Wassarman, D. A. & Rubin, G. M. Drosophila homologs of baculovirus inhibitor of apoptosis proteins function to block cell death. Cell. 83, 1253-1262 (1995).

Rothe, M., Pan, M. G., Henzel, W. J., Ayres, T. M. & Goeddel, D. V. The TNFR2-FRAF signaling complex contains two novel proteins related to baculoviral inhibitor of apoptosis proteins. Cell. 83. 1243-1252 (1995).

Mastrangelo, A. J. & Betenbaugh, M. J. Implications and applications of apoptosis in cell culture. Current Opinion in Biotechnology. 6, 198-202 (1995).

Harvey, A. J., Bidwai, A. P. & Miller, L. K. Doom, a Product of the Drosophila mod(mdg4) Gene, Induces Apoptosis and Binds to Baculovirus Inhibitor-of-Apoptosis Proteins. Molecular and cellular biology 17, 2835 (1997).

Seshagiri, S. & Miller, L. K. Caenorhabditis elegans CED-4 stimulates CED-3 processing and CED-3-induced apoptosis. Current Biology. 7, 455-460 (1997).

Vucic, D., Seshagiri, S. & Miller, L. K. Characterization of reaper- and FADD-induced apoptosis in a lepidopteran cell line. Molecular and Cellular Biology. 17, 667-676 (1997).

Hawkins, C. J., Uren, A. G., Hacker, G., Medcalf, R. L. & Vaux, D. L. Inhibition of interleukin 1 beta-converting enzyme-mediated apoptosis of mammalian cells by baculovirus IAP. Proc Natl Acad Sci U S A 93, 13786-13790 (1996).

McLachlin, J. R. & Miller, L. K. Stable transformation of insect cells to coexpress a rapidly selectable marker gene and an inhibitor of apoptosis. In Vitro Cell Dev Biol Anim 33, 575-579 (1997).

Vucic, D., Kaiser, W. J., Harvey, A. J. & Miller, L. K. Inhibition of reaper-induced apoptosis by interaction with inhibitor of apoptosis proteins (IAPs). Proc Natl Acad Sci U S A 94, 10183-10188 (1997).

Miller, L. K. Baculovirus interaction with host apoptotic pathways. J Cell Physiol 173, 178-182 (1997).

Seshagiri, S. & Miller, L. K. Baculovirus inhibitors of apoptosis (IAPs) block activation of Sf- caspase-1. Proc Natl Acad Sci U S A 94, 13606-13611 (1997).

Vucic, D., Kaiser, W. J. & Miller, L. K. Inhibitor of apoptosis proteins physically interact with and block apoptosis induced by Drosophila proteins HID and GRIM. Mol Cell Biol 18, 3300-3309 (1998).

Seshagiri, S., Chang, W. T. & Miller, L. K. Mutational analysis of Caenorhabditis elegans CED-4. FEBS Lett 428, 71-74 (1998).

Resnicoff, M. et al. The baculovirus anti-apoptotic p35 protein promotes transformation of mouse embryo fibroblasts. J Biol Chem 273, 10376-10380 (1998).

Manji, G. A., Hozak, R. R., LaCount, D. J. & Friesen, P. D. Baculovirus inhibitor of apoptosis functions at or upstream of the apoptotic suppressor P35 to prevent programmed cell death. J Virol 71, 4509-4516 (1997).

LaCount, D. J. & Friesen, P. D. Role of early and late replication events in induction of apoptosis by baculoviruses. J Virol 71, 1530-1537 (1997).

Clem, R. J. et al. Modulation of cell death by Bcl-XL through caspase interaction. Proc Natl Acad Sci U S A 95, 554-559 (1998).

Bergmann, A., Agapite, J. & Steller, H. Mechanisms and control of programmed cell death in invertebrates. Oncogene 17, 3215-3223 (1998).

Kaiser, W. J., Vucic, D. & Miller, L. K. The Drosophila inhibitor of apoptosis D-IAP1 suppresses cell death induced by the caspase drICE. FEBS Lett 440, 243-248 (1998).

Vucic, D., Kaiser, W. J. & Miller, L. K. A mutational analysis of the baculovirus inhibitor of apoptosis Op-IAP. J Biol Chem 273, 33915-33921 (1998).

Sah, N. K. et al. The baculovirus antiapoptotic p35 gene also functions via an oxidant-dependent pathway [In Process Citation]. Proc Natl Acad Sci U S A 96, 4838-4843 (1999).

Izquierdo, M. et al. Blocked negative selection of developing T cells in mice expressing the baculovirus p35 caspase inhibitor. Embo J 18, 156-166 (1999).

Bose, R. et al. Ceramide generation by the Reaper protein is not blocked by the caspase inhibitor, p35. J Biol Chem 273, 28852-28859 (1998).

Lee, J. C., Chen, H. H. & Chao, Y. C. Persistent baculovirus infection results from deletion of the apoptotic suppressor gene p35. J Virol 72, 9157-9165 (1998).

Zhou, Q. et al. Interaction of the baculovirus anti-apoptotic protein p35 with caspases. Specificity, kinetics, and characterization of the caspase/p35 complex. Biochemistry 37, 10757-10765 (1998).

Morishima, N., Okano, K., Shibata, T. & Maeda, S. Homologous p35 proteins of baculoviruses show distinctive anti-apoptotic activities which correlate with the apoptosis-inducing activity of each virus. FEBS Lett 427, 144-148 (1998).

Seshagiri, S. & Miller, L. K. Baculovirus inhibitors of apoptosis (IAPs) block activation of Sf-caspase-1. Proc Natl Acad Sci U S A 94, 13606-13611 (1997).

Griffiths, C. M. et al. In vitro host range Autographa californica nucleopolyhedrovirus recombinants lacking functional p35, iap1 or iap2. J Gen Virol 80, 1055-1066 (1999).

Ekert, P. G., Silke, J. & Vaux, D. L. Inhibition of apoptosis and clonogenic survival of cells expressing crmA variants: optimal caspase substrates are not necessarily optimal inhibitors. Embo J 18, 330-338 (1999).

Du, Q., Lehavi, D., Faktor, O., Qi, Y. & Chejanovsky, N. Isolation of an apoptosis suppressor gene of the *Spodoptera littoralis* nucleopolyhedrovirus. J Virol 73, 1278-1285 (1999).

Dai, X., Shi, X., Pang, Y. & Su, D. Prevention of baculovirus-induced apoptosis of BTI-Tn-5Bl-4 (Hi5) cells by the p35 gene of Trichoplusia ni multicapsid nucleopolyhedrovirus. J Gen Virol 80, 1841-1845 (1999).

Miller, L. K. An exegesis of IAPs: salvation and suprises from BIR motifs. Trends Cell Biol 9, 323-328 (1999).

Rhee, W. J., Kim, E. J. & Park, T. H. Kinetic Effects of Silkworm Hemolymph on the Delayed Host Cell Death in an Insect Cell-Baculovirus System. Biotechnol Prog 15, 1028-1032 (1999).

Accession No. L22858, Autographa Californiica Nuclear Polyhedrosis Virus Clone C6, Complete Genome, Nucleotide Query.

Mastrangelo, A J et al. "Overcoming Apoptosis: New Method For Improving Protein-Expression Systems" Trends in Biotechnology, Elsevier Publications, Cambridge, GB, vol. 16, No. 2, Feb. 1, 1998, p. 88-95.

Al-Rubeai, Mohamed et al.: "Apoptosis in Cell Culture." Current Opinion in Biotechnology, vol. 9, No. 2, Apr. 1998, pp. 152-156.

Mitchell-Logean, Christine et al., "Bcl-2 Expression in Spodoptera Frugiperda Sf-9 and Trichoplusia ni BTI-Tn-5B1-4 Insect Cells: Effect on Recombinant Protein Expression and Cell Viability" Biotechnol Bioeng; Biotechnology and Bioengineering. Nov. 20, 1997, John Wiley & Sons Inc., New York NY, vol. 56, No. 4, pp. 380-390.

Database WPI, Section Ch, Week 199735, Derwent Publications Ltd., London GB;, An 1997-380167, Jun. 26, 1997. Abstract.

Suzuki, E et al. "Establishing Apoptosis Resistant Cell Lines For Improving Protein Productivity of Cell Culture." Cytotechnology, Kluwer Academic Publishers, Dordrecht, NL, vol. 23, No. 1-3, 1997, pp. 55-59.

SEQUENCE LISTING

```
<160> NUMBER OF SEQ ID NOS: 11

<210> SEQ ID NO 1
<211> LENGTH: 900
<212> TYPE: DNA
<213> ORGANISM: Autographa californica nucleopolyhedrovirus
<220> FEATURE:
<221> NAME/KEY: CDS
<222> LOCATION: (1)..(897)
<300> PUBLICATION INFORMATION:
<301> AUTHORS: Ayres, Martin D.
      Howard, Stephen C.
      Kuzio, John
      Lopez-Ferber, Miguel
      Possee, Robert D.
<302> TITLE: The Complete DNA Sequence of Autographa californica
      Nuclear Polyhedrosis Virus
<303> JOURNAL: Virology
<304> VOLUME: 202
<305> ISSUE: 2
<306> PAGES: 586-605
<307> DATE: 1994
<308> DATABASE ACCESSION NUMBER: L22858
<309> DATABASE ENTRY DATE: 1999-03-08
<313> RELEVANT RESIDUES: 116492 TO 117391

<400> SEQUENCE: 1 atg tgt gta att ttt ccg gta gaa atc gac gtg tcc cag acg att att        48
Met Cys Val Ile Phe Pro Val Glu Ile Asp Val Ser Gln Thr Ile Ile
 1               5                  10                  15 cga gat tgt cag gtg gac aaa caa acc aga gag ttg gtg tac att aac        96
Arg Asp Cys Gln Val Asp Lys Gln Thr Arg Glu Leu Val Tyr Ile Asn
             20                  25                  30 aag att atg aac acg caa ttg aca aaa ccc gtt ctc atg atg ttt aac       144
Lys Ile Met Asn Thr Gln Leu Thr Lys Pro Val Leu Met Met Phe Asn
         35                  40                  45 att tcg ggt cct ata cga agc gtt acg cgc aag aac aac aat ttg cgc       192
Ile Ser Gly Pro Ile Arg Ser Val Thr Arg Lys Asn Asn Asn Leu Arg
     50                  55                  60 gac aga ata aaa tca aaa gtc gat gaa caa ttt gat caa cta gaa cgc       240
Asp Arg Ile Lys Ser Lys Val Asp Glu Gln Phe Asp Gln Leu Glu Arg
 65                  70                  75                  80 gat tac agc gat caa atg gat gga ttc cac gat agc atc aag tat ttt       288
Asp Tyr Ser Asp Gln Met Asp Gly Phe His Asp Ser Ile Lys Tyr Phe
                 85                  90                  95 aaa gat gaa cac tat tcg gta agt tgc caa aat ggc agc gtg ttg aaa       336
Lys Asp Glu His Tyr Ser Val Ser Cys Gln Asn Gly Ser Val Leu Lys
            100                 105                 110 agc aag ttt gct aaa att tta aag agt cat gat tat acc gat aaa aag       384
Ser Lys Phe Ala Lys Ile Leu Lys Ser His Asp Tyr Thr Asp Lys Lys
        115                 120                 125
```

```
tct att gaa gct tac gag aaa tac tgt ttg ccc aaa ttg gtc gac gaa      432
Ser Ile Glu Ala Tyr Glu Lys Tyr Cys Leu Pro Lys Leu Val Asp Glu
    130                 135                 140 cgc aac gac tac tac gtg gcg gta tgc gtg ttg aag ccg gga ttt gag      480
Arg Asn Asp Tyr Tyr Val Ala Val Cys Val Leu Lys Pro Gly Phe Glu
145                 150                 155                 160 aac ggc agc aac caa gtg cta tct ttc gag tac aac ccg att ggt aac      528
Asn Gly Ser Asn Gln Val Leu Ser Phe Glu Tyr Asn Pro Ile Gly Asn
                165                 170                 175 aaa gtt att gtg ccg ttt gct cac gaa att aac gac acg gga ctt tac      576
Lys Val Ile Val Pro Phe Ala His Glu Ile Asn Asp Thr Gly Leu Tyr
    180                 185                 190 gag tac gac gtc gta gct tac gtg gac agt gtg cag ttt gat ggc gaa      624
Glu Tyr Asp Val Val Ala Tyr Val Asp Ser Val Gln Phe Asp Gly Glu
195                 200                 205 caa ttt gaa gag ttt gtg cag agt tta ata ttg ccg tcg tcg ttc aaa      672
Gln Phe Glu Glu Phe Val Gln Ser Leu Ile Leu Pro Ser Ser Phe Lys
        210                 215                 220 aat tcg gaa aag gtt tta tat tac aac gaa gcg tcg aaa aac aaa agc      720
Asn Ser Glu Lys Val Leu Tyr Tyr Asn Glu Ala Ser Lys Asn Lys Ser
225                 230                 235                 240 atg atc tac aag gct tta gag ttt act aca gaa tcg agc tgg ggc aaa      768
Met Ile Tyr Lys Ala Leu Glu Phe Thr Thr Glu Ser Ser Trp Gly Lys
                245                 250                 255 tcc gaa aag tat aat tgg aaa att ttt tgt aac ggt ttt att tat gat      816
Ser Glu Lys Tyr Asn Trp Lys Ile Phe Cys Asn Gly Phe Ile Tyr Asp
            260                 265                 270 aaa aaa tca aaa gtg ttg tat gtt aaa ttg cac aat gta act agt gca      864
Lys Lys Ser Lys Val Leu Tyr Val Lys Leu His Asn Val Thr Ser Ala
    275                 280                 285 ctc aac aaa aat gta ata tta aac aca att aaa taa                      900
Leu Asn Lys Asn Val Ile Leu Asn Thr Ile Lys
290                 295

<210> SEQ ID NO 2
<211> LENGTH: 299
<212> TYPE: PRT
<213> ORGANISM: Autographa californica nucleopolyhedrovirus

<400> SEQUENCE: 2

Met Cys Val Ile Phe Pro Val Glu Ile Asp Val Ser Gln Thr Ile Ile
1               5                   10                  15

Arg Asp Cys Gln Val Asp Lys Gln Thr Arg Glu Leu Val Tyr Ile Asn
            20                  25                  30

Lys Ile Met Asn Thr Gln Leu Thr Lys Pro Val Leu Met Met Phe Asn
        35                  40                  45

Ile Ser Gly Pro Ile Arg Ser Val Thr Arg Lys Asn Asn Leu Arg
    50                  55                  60

Asp Arg Ile Lys Ser Lys Val Asp Glu Gln Phe Asp Gln Leu Glu Arg
65                  70                  75                  80

Asp Tyr Ser Asp Gln Met Asp Gly Phe His Asp Ser Ile Lys Tyr Phe
                85                  90                  95

Lys Asp Glu His Tyr Ser Val Ser Cys Gln Asn Gly Ser Val Leu Lys
            100                 105                 110

Ser Lys Phe Ala Lys Ile Leu Lys Ser His Asp Tyr Thr Asp Lys Lys
        115                 120                 125

Ser Ile Glu Ala Tyr Glu Lys Tyr Cys Leu Pro Lys Leu Val Asp Glu
    130                 135                 140
```

Arg Asn Asp Tyr Tyr Val Ala Val Cys Val Leu Lys Pro Gly Phe Glu
145                 150                 155                 160

Asn Gly Ser Asn Gln Val Leu Ser Phe Glu Tyr Asn Pro Ile Gly Asn
            165                 170                 175

Lys Val Ile Val Pro Phe Ala His Glu Ile Asn Asp Thr Gly Leu Tyr
        180                 185                 190

Glu Tyr Asp Val Ala Tyr Val Asp Ser Val Gln Phe Asp Gly Glu
    195                 200                 205

Gln Phe Glu Glu Phe Val Gln Ser Leu Ile Leu Pro Ser Ser Phe Lys
210                 215                 220

Asn Ser Glu Lys Val Leu Tyr Tyr Asn Glu Ala Ser Lys Asn Lys Ser
225                 230                 235                 240

Met Ile Tyr Lys Ala Leu Glu Phe Thr Thr Glu Ser Ser Trp Gly Lys
            245                 250                 255

Ser Glu Lys Tyr Asn Trp Lys Ile Phe Cys Asn Gly Phe Ile Tyr Asp
        260                 265                 270

Lys Lys Ser Lys Val Leu Tyr Val Lys Leu His Asn Val Thr Ser Ala
    275                 280                 285

Leu Asn Lys Asn Val Ile Leu Asn Thr Ile Lys
290                 295

```
<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 3
ctagaagttg gaaagatgcc agcggctggt cgtaatag                              38

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 4
ctagctatta cgaccagccg ctggcatctt tccaactt                              38

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: p35upEcoRI
      primer

<400> SEQUENCE: 5
cagaattcat gtgtgtaatt tttccggtag                                       30

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence:
      p35lowXbaI-NO stop primer
```

-continued

```
<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence:
      p35lowXbaI-Stop primer

<400> SEQUENCE: 6
ttttgctcta gatttaattg tgtttaatat tac                           33

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence:
      p35lowXbaI-Stop primer

<400> SEQUENCE: 7
aatgctctag attatttaat tgtgtttaat attac                         35

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence:
      p166-p35 linker DNA

<400> SEQUENCE: 8
ttaaacacaa ttaaa                                               15

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:
      p166-p35 linker polypeptide

<400> SEQUENCE: 9

Leu Asn Thr Ile Lys
1               5

<210> SEQ ID NO 10
<211> LENGTH: 54
<212> TYPE: DNA
<213> ORGANISM: Artificial Sequence
<220> FEATURE:
<223> OTHER INFORMATION: Description of Artificial Sequence:
      p166-p35-AcV5 linker DNA

<400> SEQUENCE: 10
ttaaacacaa ttaaatctag aagttggaaa gatgccagcg gctggtcgta atag    54

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence:
      p166-p35-AcV5 linker polypeptide

<400> SEQUENCE: 11

Leu Asn Thr Ile Lys Ser Arg Ser Trp Lys Asp Ala Ser Gly Trp Ser
1               5                   10                  15
```

STABLE CELL LINES RESISTANT TO APOPTOSIS AND NUTRIENT STRESS AND METHODS OF MAKING SAME

BACKGROUND OF THE INVENTION

1. Field of the Invention

The invention pertains to the field of baculovirus expression. More particularly, the invention pertains to novel cell lines resistant to apoptosis and nutrient stresses.

2. Description of Related Art

The baculovirus expression vector system is one of the most effective and widely used eukaryotic protein expression systems available. In the baculovirus expression system, foreign genes are inserted into the baculovirus genome and are typically expressed under the transcriptional control of one of the hyper-expressed baculovirus very late promoters, polyhedrin or p10. In addition to very high-level protein production, an additional advantage of the baculovirus expression system is the quality of post-translational processing of proteins. Foreign proteins expressed in baculovirus-infected insect cells are post-translationally processed in a manner very similar if not identical to that observed for proteins translated in other higher eukaryotes, particularly vertebrates. The baculovirus system is especially useful for production of secreted and membrane-bound proteins from higher eukaryotes since protein folding and processing in the baculovirus system is typically similar to other higher eukaryotes and usually results in biologically active proteins. However, some post-translational processes, such as trimming and modification of complex carbohydrates, differ from those observed in vertebrate cells.

Protein production in this expression system occurs in the context of a lethal infection. Thus, the physiological state of the host cell during infection may influence the level of recombinant protein translation, protein processing, and protein trafficking or secretion. Factors which influence host cell health or viability could influence protein production and quality, as well as the overall utility of this expression system. The health, growth, and propagation of host cells prior to infection by recombinant baculoviruses is also an important practical concern for large scale production of proteins in the baculovirus system.

An integral component of baculovirus expression technology is the insect cell line in which recombinant proteins are expressed. Desirable characteristics for such cell lines include the capacity to scale cultures to high cell densities, cell growth in serum free medium, growth in suspension cultures, and high level protein expression. Two cell lines, Sf9 and Sf21, are routinely used since these cells grow to high density, express reasonably high levels of protein, adapt well to serum-free media formulations, and are easily adapted to large scale suspension cultures. Sf9 cells are a derivative of the Sf21 line.

It has been demonstrated that *Autographa californica* nucleopolyhedrovirus (AcMNPV) infection induces apoptosis in Sf21 cells if the AcMNPV p35 gene is inactivated or absent (Clem, R. J. et al., 1991, Hershberger, P. A. et al., 1994). Numerous subsequent studies further characterized the role and function of the P35 protein as a potent general suppressor of apoptosis (Rabizadeh, S. et al., 1993, Sugimoto, A. et al., 1994, Hay, B. A. et al., 1994, Beidler, D. R. et al., 1995, Martinou, I. et al., 1995, Robertson, N. M. et al., 1997).

The P35 protein inhibits programmed cell death by inhibiting cellular caspases, a family of cysteinyl proteases that are important components or effectors of the cell death pathway (Martin, S. J. and Green, D. R., 1995, Cryns, V. and Yuan, J., 1998). P35 has been shown to inhibit caspases belonging to groups I, II, and III and inhibition is believed to result from a multistep mechanism. P35 interacts directly with cellular caspases and is cleaved (at aspartate 87) by the caspase (Xue, D. and Horvitz, H. R., 1995, Bertin, J. et al., 1996, Bump, N. J. et al., 1995, Fisher, A. J. et al., 1999).

Cleavage of P35 is believed to result in a conformational change that is required for P35 inhibition of the caspase. Thus, P35 appears to represent an irreversible inhibitor of caspases since P35 fragments of 10 and 25 kDa remain associated with the caspase after cleavage at P35 residue Asp87 (Bump, N. J. et al., 1995, Fisher, A. J. et al., 1999).

However, P35 cleavage alone does not appear to be sufficient for inhibition of caspase activity since a single amino acid substitution mutation in P35 prevents the stable association of P35 with the caspase (but not its cleavage), and P35 containing this mutation does not inhibit caspase-3 activity (Fisher, A. J., et al. 1999).

A previous study showed that the P35 protein expressed in stable cell lines was capable of inhibiting apoptosis induced by actinomycin D or by a mutant virus in which the p35 gene was deleted (Cartier, J. L., et al. 1994). In that study, stably transfected cells expressing p35 did not appear to have increased viability after infection, when compared with untransfected Sf21 cells. Resistance of those p35 expressing cells to nutrient stress was not examined, nor was the expression of secreted proteins from baculovirus expression vectors examined.

A mammalian oncogene, bc1-2, is normally expressed in the T and B-lymphocytes. It is believed that the product of this gene is a "survival gene" normally involved in enhancing cellular survival. Bc1-2 has been stably transfected into an immortalized cell line (Milner et al., 1992). The stable transfectants were selected using G418.

Another study utilized these bc1-2 expressing cell lines to test for survival of these cells under apoptotic and high stress conditions (Singh et al., 1996). The growth characteristics of the bc1-2 overexpressing cell lines were compared with control cells in stationary, suspension and serum-free cultures. In each of these cases, bc1-2 suppressed apoptosis and the cells were more robust than the control cells. This study concentrated on overexpressing bc1-2, a mammalian protein that is otherwise normally expressed in the cells. No viral genes encoding suppressors of apoptosis were incorporated into the cell lines. Bc1-2 is a suppressor of apoptosis that is expressed normally from mammalian cells and does not block apoptosis as broadly as certain viral suppressors of apoptosis, such as baculovirus P35, Cowpox CrmA or Vaccinia SPI-2. Thus, the use of viral suppressors of apoptosis may provide substantial advantages over cellular proteins. In the former study of bc1-2 expressing cells, only cell growth and responses to modified nutrient regimes were examined. They did not examine the effects of apoptotic suppression on foreign gene expression or on protein production.

*Spodoptera frugiperda* Sf9 cells provide desirable growth characteristics and are extensively used in both industrial and research applications. In general, recombinant protein expression in insect cells infected with baculovirus expression vectors is much higher than in mammalian cells infected with vertebrate virus expression vectors. Sf9 cells, as well as most insect cell lines, are limited by their susceptibility to stress which results in the induction of apoptosis. Another widely used cell line derived from *Trichoplusia ni* (BTI-Tn5B1-4 or HighFive™ cells) provides greatly improved protein expression but is more difficult to grow in suspension cultures, and may not be suitable for some types of scale-up applications. Sf9 cells do not generate the same high levels of protein expression that can be achieved from Tn5B1-4 cells. Thus, neither of these cell lines provides the optimal combination of features for high-level protein production.

SUMMARY OF THE INVENTION

Cell lines that are commonly used for protein expression are engineered to include genes that encode suppressors of apoptosis (SA). Insect cell lines expressing these SA genes are resistant to apoptosis or programmed cell death, and have an increased capacity to express certain recombinant proteins. These cell lines also have increased resistance to many types of stress. Because some of the SA proteins inhibit apoptosis in a wide spectrum of organisms, these genes may be inserted into other plant or animal cell lines for a variety of purposes involving resistance to apoptosis or resistance to stress.

The cell lines of this invention have been stably transfected with a plasmid containing a gene for a suppressor of apoptosis. This gene is preferably the p35 gene from a baculovirus such as AcMNPV. The cell lines are resistant to both exposure to an inducer of apoptosis, such as actinomycin D, and nutrient deprivation. These cell lines also produced increased levels of recombinant proteins compared to the parental cell lines from which they were derived.

Cell lines expressing a suppressor of apoptosis, such as P35 or a tagged form of P35, are generated by a method of the invention. First, a gene for the suppressor of apoptosis is isolated. Then, a recombinant DNA expression vector is constructed to contain the suppressor of apoptosis gene. The recombinant DNA expression vector is capable of expressing the gene in a host. The plasmid is transfected into a host cell. The host cells are exposed to an inducer of apoptosis, such as actinomycin D. Those cells which survive exposure to the inducer of apoptosis are then cloned to create an apoptosis-resistant cell line. In a preferred embodiment, the recombinant DNA expression vector is cotransfected with a second recombinant DNA expression vector containing a selectable marker, such as an antibiotic resistance gene. The second recombinant DNA expression vector is used to eliminate cells which have not been successfully transfected prior to selection with an inducer of apoptosis.

DETAILED DESCRIPTION OF THE INVENTION

Figure 1:
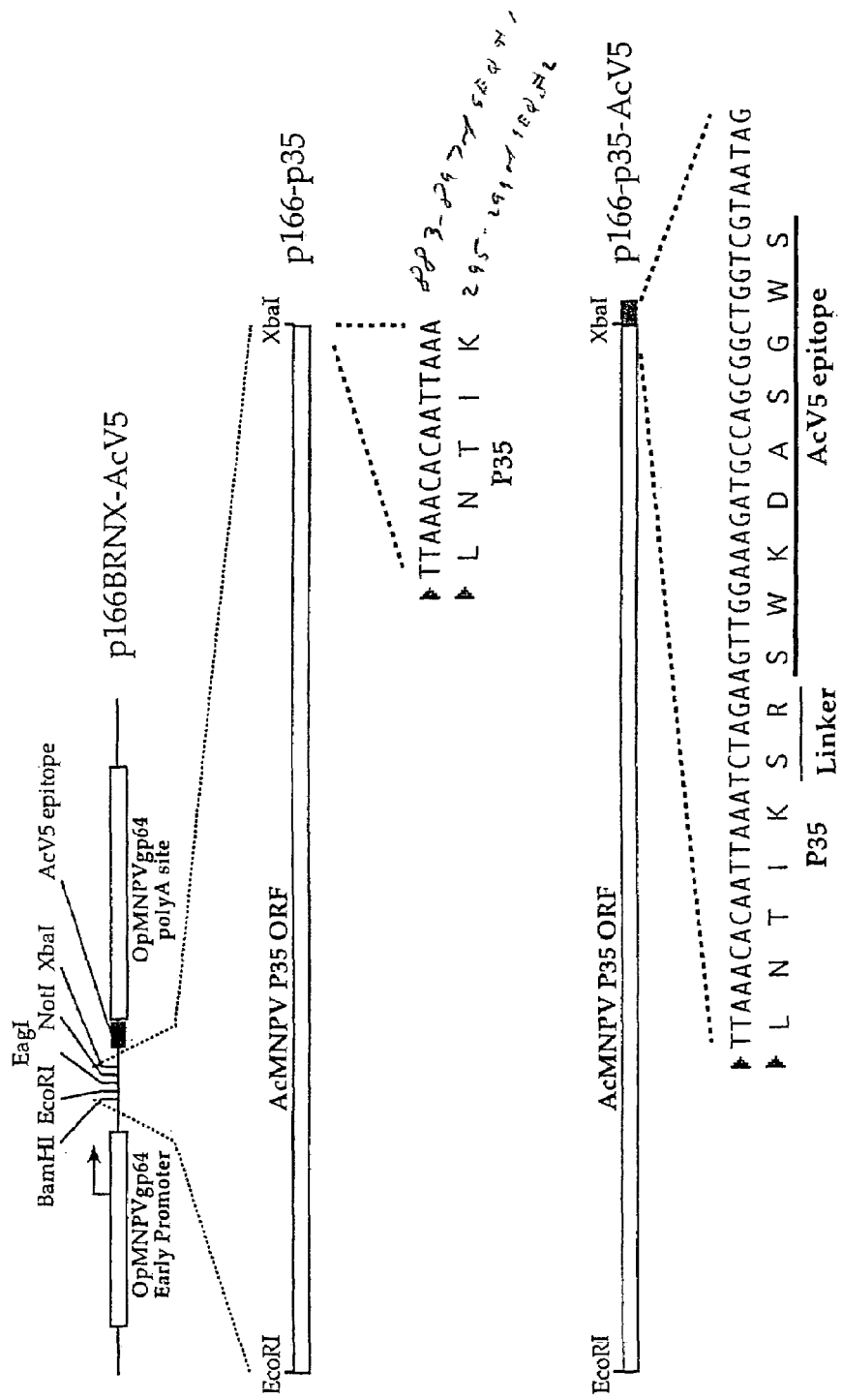
FIG. 1 shows insect cell expression (SEQ ID NO:8-11) constructs designed for expressing native and AcV5-tagged P35 proteins.

The present invention satisfies the need in the art for improved cell lines resistant to apoptosis. The baculovirus AcMNPV encodes a suppressor of apoptosis, P35, which is expressed early during the infection cycle and is known to inhibit apoptosis triggered by AcMNPV infection of Sf21 cells. Transient expression of P35 in Sf21 insect cells is also known to prevent apoptosis. Since the baculovirus already contains a p35 gene, it is not intuitive to assume that, by adding this gene to an insect cell line, it would confer the observed benefits to the infected cells. Therefore, isolating a suppressor of apoptosis from a baculovirus and incorporating it into a cell line for this purpose is novel.

Sf9 cells were engineered to express P35, a baculovirus suppressor of apoptosis. The resulting P35-expressing cells were placed under selection using an inducer of apoptosis, such as actinomycin D. Cell lines cloned by this procedure expressed P35, were more highly resistant to nutrient stress, and yielded secreted recombinant proteins from baculovirus infections at levels similar to that achieved by Tn5B1-4 cells, currently one of the best cell lines available for recombinant protein production from baculovirus-infected cells.

To generate cell lines resistant to induction of apoptosis by stressful culture conditions, and to examine the effects of constitutive cellular P35 expression on protein production from baculovirus expression vectors, cell lines expressing AcMNPV P35 or an epitope-tagged P35 fusion protein were generated. Cell lines expressing P35 were first selected using a neomycin resistance gene and G418, then selected again in the presence of actinomycin D, an inducer of apoptosis in Sf9 cells.

Several clonal isolates were generated and examined for a) resistance to actinomycin D induced apoptosis and nutrient deprivation, b) growth in various media, and c) baculovirus expression of intracellular and secreted proteins. When compared with wild type Sf9 cells, two P35 expressing cell lines showed increased resistance to actinomycin D induced apoptosis, and a marked resistance to nutrient deprivation. When these cell lines were infected with a recombinant baculovirus expressing a secreted glycoprotein (Secreted Alkaline Phosphatase, SEAP), expression of the glycoprotein from these cells exceeded expression from wild type Sf9 cells, and was comparable to expression levels obtained from Tn5B1-4 cells. Proteins expressed in these cells may also be of higher quality, as protein processing may be, on average, more uniform or more complete than in the parental cells.

Cell Line Construction

The AcMNPV p35 gene (SEQ. ID. NO. 1; Ayres, M. D. et al., 1994) was amplified from the AcMNPV genome and subcloned into an insect cell expression plasmid (p166BRNX) which contains an optimized baculovirus early promoter (Blissard, G. W. and Rohrmann, G. F., 1991, Monsma, S. A., Oomens, A. G. P. and Blissard, G. W., 1996). Although P35 may have more powerful inhibitory effects than other SAs, other suppressors of apoptosis, which include Bombyx mori P35 and inhibitors of apoptosis proteins (IAPs) from other baculoviruses, can be used similarly in the development of novel cell lines. Each of these SAs is derived from a baculovirus, and is not a part of the genome of the parental cell line. Two P35 insect cell expression plasmid constructs were generated. In one construct, the wild type AcMNPV P35 gene was cloned in its native form (amino acids 1-299). A second construct encoded the full length P35 ORF with an AcV5 epitope tag (Monsma, S. A. and Blissard, G. W., 1995)

fused to the C-terminus of P35 (FIG. 1). The P35 amino acid sequence is shown in SEQ. ID. NO. 1 and SEQ. ID. NO. 2 (Ayres, M. D. et al., 1994).

A plasmid (p166BRNX-AcV5) for insect cell expression was constructed from the OpMNPV gp64 promoter region, a multiple cloning site, sequences encoding the AcV5 epitope, and polyA addition sequences from the OpMNPV gp64 gene (FIG. 1). The AcMNPV P35 ORF was PCR amplified and cloned into the EcoRI and XbaI sites. To construct this plasmid, a complementary oligonucleotide pair (SEQ. ID. NO. 3 and SEQ. ID. NO. 4) encoding a 5' Xba I site, the AcV5 epitope (SWKDASGWS; Monsma, S. A. and Blissard, G. W. 1995), two stop codons, and an XbaI compatible cohesive end at the 3' end was synthesized and cloned into plasmid vector p166BRNX digested with XbaI. The resulting plasmid, p166BRNX-AcV5, contains a 166 nucleotide OpMNPV GP64 early promoter region (Blissard, G. W. and Rohrmann, G. F., 1991) followed by a multiple cloning site containing BamHI, EcoRI, EagI, NotI, and XbaI sites, plus a polyadenylation signal from the OpMNPV gp64 gene. This plasmid was used to create the constructs below.

The P35 ORF was cloned in frame with the AcV5 epitope such that the expressed P35 protein contains a 2 amino acid linker and a 9 amino acid AcV5 epitope at the C-terminus (FIG. 1). The AcMNPV p35 ORF (with no stop codon) was amplified by PCR from AcMNPV genomic DNA using two primers, p35upEcoRI (SEQ. ID. NO. 5, a primer that contained the sequences from the 5' end of the P35 ORF plus an EcoRI site at the 5' end) and p35lowXbaI-NO stop (SEQ. ID. NO. 6, a primer that contains sequences from the 3' end of the P35 ORF, but no stop codon, and a 3' XbaI site). The PCR product was cloned into EcoRI/XbaI digested plasmid p166BRNX-AcV5 to obtain plasmid p166-p35-AcV5. Plasmid p166-p35-AcV5 contains the p35 ORF fused to a C-terminal AcV5 epitope tag, under the control of the OpMNPV gp64 early promoter (FIG. 1).

Construct p166-p35 includes a stop codon upstream of the AcV5 epitope and expresses a native P35 protein (FIG. 1). The p35 gene was amplified using primers p35upEcoRI (SEQ. ID. NO. 5) and p35lowXbaI-Stop (SEQ. ID. NO. 7) using the same strategy described above, except that the P35 stop codon was included in the 3' oligonucleotide and PCR product (FIG. 1). The resulting plasmid, p166-p35, expresses wild type P35. All of the constructs were confirmed by DNA sequencing.

Selection of Stably Transfected Cell Lines

Each P35 expression plasmid was cotransfected into Sf9 insect cells with a plasmid (pIE1-Neo) expressing Neomycin Phosphotransferase (NPT) and cells were selected using Geneticin disulfate (G418). Plasmid pIE1-Neo contains a bacterial NPT gene under the control of an AcMNPV IE1 promoter (Monsma, S. A., Oomens, A. G. P. and Blissard, G. W., 1996). Cells were also cotransfected with plasmid p166-EGFP, which contains an enhanced green fluorescent protein gene under the transcriptional control of the OpMNPV gp64 early promoter (Chang, M. J., Kuzio, J. and Blissard, G. W., 1999). EGFP expression was used as a convenient visible marker for transgene expression in stably transfected cell lines. Other parental cell lines available for production of stably transfected cell lines include IPLB-Sf21, BTI-Tn5B1-4, BTI-MG-1, Tn368, Ld652Y, and BTI-EAA, any cell lines derived from the cell lines listed here, as well as any cell lines susceptible to baculovirus infection. Those skilled in the art would appreciate that, in order to meet their unique expression needs, this method is applicable to cell lines not specifically listed. Examples of some of these cell lines are found in Granados, R. R. and Hashimoto, Y., 1989.

Sf9 cells were transfected using the $CaPO_4$ technique being known in the art, and herein incorporated by reference (Blissard, G. W. and Rohrmann, G. F., 1991). To generate cells expressing the epitope tagged P35 protein, Sf9 cells ($2 \times 10^6$ cells) were transfected with plasmids pIE1-Neo (1 µg), p166-p35-AcV5 (5 µg), and p166-EGFP (1 µg). To generate cells expressing the native P35 protein, Sf9 cells were similarly transfected with plasmids pIE1-Neo (1 µg), p166-p35 (5 µg), and p166EGFP (1 µg). At 48 hours post transfection, G418 was added to the medium to a final concentration of 1 mg/ml and cells were incubated in G418 containing medium for three to four weeks. Under these conditions, only Sf9 cells that were stably transfected survived. Cells selected in G418 were also screened visually for EGFP fluorescence. Untransfected Sf9 cells were used as a negative control.

In order to select cells expressing higher levels of functional P35, the surviving transfected cells were placed in medium containing 0.1 µg/ml actinomycin D for 1 hour. Another example of an inducer of apoptosis that could be used to select cells resistant to apoptosis is UV irradiation. In mammalian cells, inducers of apoptosis such as tumor necrosis factor (TNF) could also be used. The selection using an inducer of apoptosis could alternatively be performed without cotransfection with a selectable marker such as an antibiotic resistance gene.

At the end of the one hour incubation in actinomycin D, the medium was replaced with fresh TNMFH medium (containing no actinomycin D) and cells were allowed to grow for three days. After three days, 85-90% of the cells treated with actinomycin D-containing medium died. Medium was replaced after 3 days and surviving single cells formed small colonies which were subsequently propagated and used to clone individual cell lines by limiting dilution. For limiting dilution cloning, cells were diluted into 96 well plates such that each well received only one cell on average. Each well was subsequently monitored to ensure that only a single colony was present. Monoclonal cell lines were selected and propagated. Cell lines expressing the native P35 protein were named $Sf9^{P35}$, and lines expressing the epitope tagged P35 protein were named $Sf9^{P35AcV5}$. Five stable cell lines expressing P35 were selected and named $Sf9^{P35-1}$, $Sf9^{P35-2}$, $Sf9^{P35-3}$, $Sf9^{P35-4}$, and $Sf9^{P35-5}$. Three cloned cell lines expressing the epitope tagged P35 protein were selected and named $Sf9^{P35AcV5-1}$, $Sf9^{P35AcV5-2}$, and $Sf9^{P35AcV5-3}$.

A sample of two new cell lines, designated BTI-Sf9-P35AcV5-1 and BTI-Sf9-P35AcV5-3, was deposited on Feb. 23, 2001 with the American Type Culture Collection, at 10801 University Blvd., Manassas, Va. 20110-2209, under accession No. PTA-3099 and No. PTA-3100.

Growth Rates (in Serum-Containing Medium)

Growth rates of selected cell lines were determined by plating $1 \times 10^6$–$2 \times 10^6$ cells in TNMFH medium supplemented with 10% fetal bovine serum in T-25 flasks, and monitoring cell growth at 24 hours intervals by a technique being known in the art, and herein incorporated by reference (Wang, P., Granados, R. R. and Shuler, M. L., 1992).

Growth curves were generated for cell lines $Sf9^{P35-1}$, $Sf9^{P35-3}$, $Sf9^{P35-4}$ and $Sf9^{P35-5}$, $Sf9^{P35AcV5-1}$, $Sf9^{P35AcV5-2}$, and $Sf9^{P35AcV5-3}$. To determine whether the growth rates of cell lines expressing P35 were affected by P35 expression or stable transfection, the growth curves were compared to the growth rate of Sf9 cells (Table 1). Under these conditions, the average doubling time for unmodified Sf9 cells was approximately 26 hours. Doubling times for stably transformed cell lines ranged from 23 to 39 hours, with most lines showing similar doubling times to Sf9 cells. Only cell lines Sf9$^{P35-3}$ and Sf9$^{P35-4}$ showed growth rates that were significantly extended in comparison to the parental Sf9 cell line.

TABLE 1

| | Growth rates of cell lines expressing P35 | | | | | | | |
|---|---|---|---|---|---|---|---|---|
| Cell line | Sf9 | Sf9$^{P35-1}$ | Sf9$^{P35-3}$ | Sf9$^{P35-4}$ | Sf9$^{P35-5}$ | Sf9$^{P35AcV5-1}$ | Sf9$^{P35AcV5-2}$ | Sf9$^{P35AcV5-3}$ |
| Doubling Time (h) | 26 | 24 | 31 | 39 | 27 | 27 | 23 | 25 |

Baculovirus Expression and Reporter Gene Analysis

The novel cell lines may also preferably contain a recombinant DNA for expression of a recombinant protein. For example, two recombinant baculovirus constructs that express well characterized proteins were used to compare recombinant protein production in the cells stably transfected with P35 with production from standard insect cell lines. Virus rAcMNPV-SEAP encodes a truncated human placental alkaline phosphatase gene under the control of the AcMNPV polyhedrin promoter (Davis, T. R., Trotter, K. M., Granados, R. R. and Wood, H. A., 1992). This virus expresses secreted alkaline phosphatase (SEAP), a glycoprotein that is conveniently monitored by measuring SEAP activity from cell culture supernatants (Davis, T. R. et al., 1993). A second virus, AcMNPV-246 (Wickham, T. J., Davis, T., Granados, R. R., Shuler, M. L. and Wood, H. A., 1992), contains an *E. coli* LacZ gene under the control of the AcMNPV polyhedrin promoter. Beta-galactosidase assays of infected cell lysates were used to measure the synthesis of this intracellular protein.

Secreted Alkaline Phosphatase (SEAP) Expression in Serum-Containing Media

To examine levels of SEAP expression from Sf9 or stably transfected cells expressing P35 in serum-containing medium, cells were plated in 24 well plates. For Sf9 cells and stably transfected cells expressing P35, 3×10$^5$ cells/well were plated in each well of 24 well plates. Due to their larger size, Tn5B1-4 (HighFive™) cells were plated at a density of 1×10$^5$ cells/well.

Figure 2:
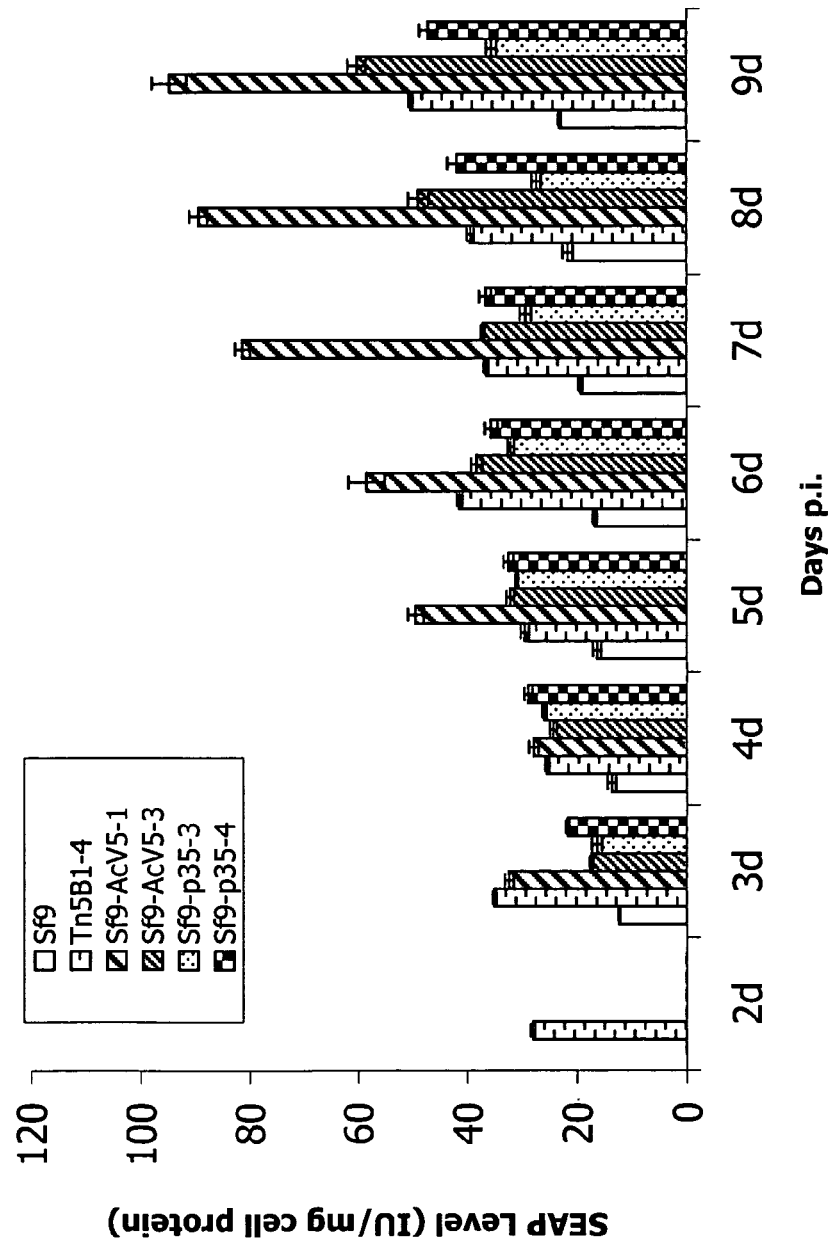
FIG. 2 shows secreted alkaline phosphatase (SEAP) levels measured from the supernatants of various cell lines infected with virus rAcMNPV-SEAP and grown in TNMFH medium containing 10% fetal bovine serum (FBS).

Cells were infected with rAcMNPV-SEAP at a multiplicity of infection (MOI) of 10 for 1 hour, then virus was removed and cells were placed in fresh medium. Supernatants were collected from infected cells at 2, 3, 4, 5, 6, 7, 8, or 9 days post infection (p.i.). Each time point in FIG. 2 represents SEAP accumulation from initiation of infection through the indicated time. For each time point, three separate replicate wells were infected and separate supernatants collected. SEAP activity was determined by a technique being known in the art, and herein incorporated by reference (Davis, T. R., Trotter, K. M., Granados, R. R. and Wood, H. A., 1992). Tn5B1-4 cells are substantially larger than Sf9 cells. Therefore, to accurately compare expression of SEAP from stably transfected Sf9 cells with that from Tn5B1-4 cells, SEAP activity was calculated on both a "per cell" and a "per biomass" basis and examined as: 1) international units (IU)/cell and 2) IU/mg cell protein. The total biomass of the Sf9 and Tn5BI-4 cells were compared using total protein content per cell to indicate biomass.

As estimated from Bradford protein assays, Tn5B1-4 cells contained approximately 0.353 mg protein per 10$^6$ cells, whereas Sf9$^{P35AcV5-1}$ cells (a representative cell line derived from Sf9 cells) contained approximately 0.208 mg protein per 10$^6$ cells. Thus, based on protein content, the biomass of an average Tn5B1-4 cell is almost 1.5 times that of an average Sf9 cell. Levels of SEAP were determined and are presented as International Units (IU) SEAP per mg cell protein (IU/mg cell protein) in FIG. 2. As expected, SEAP expression from Tn5BI-4 cells exceeded that from Sf9 cells, at most times by approximately 2-3 fold when compared on a biomass basis (FIG. 2, 3-9 days post infection).

Figure 3:
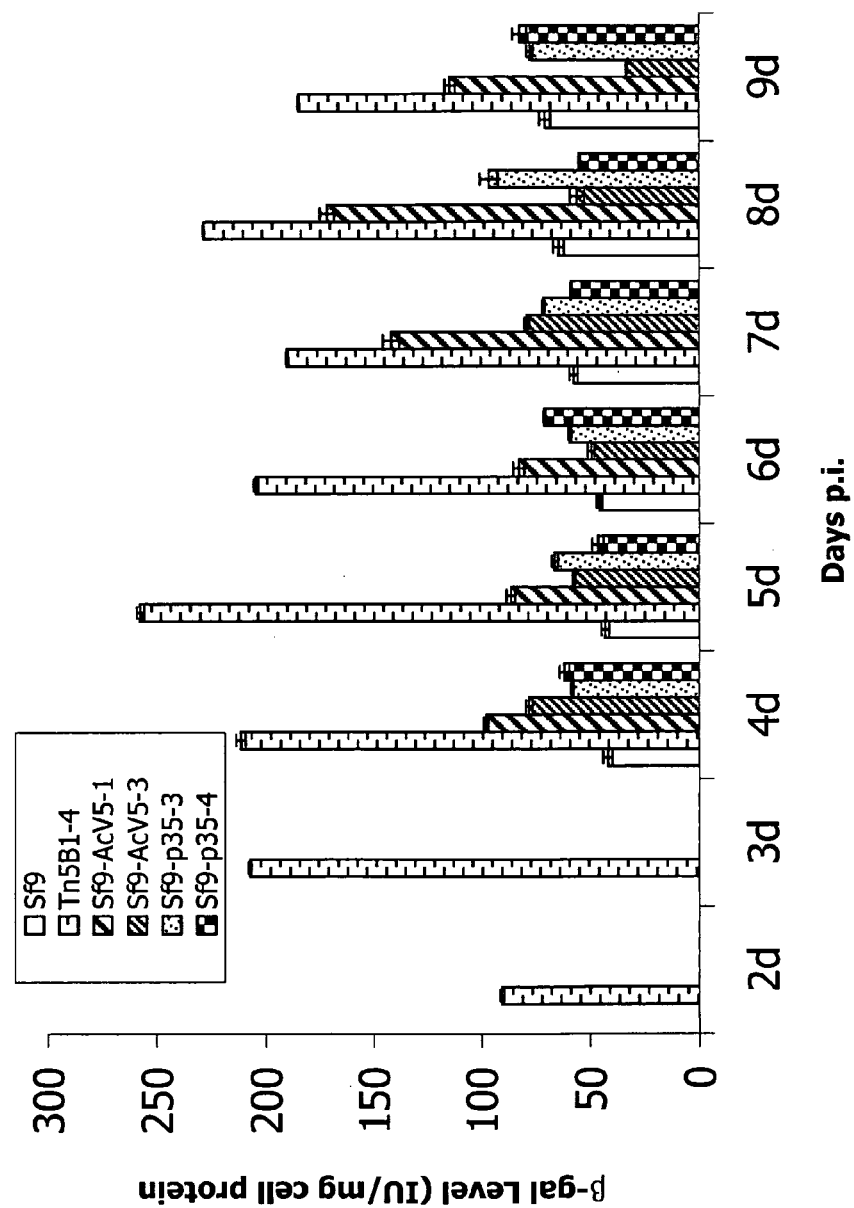
FIG. 3 shows beta-galactosidase levels measured from cellular extracts of various cell lines infected with virus AcMNPV-246 and grown in TNMFH medium containing 10% FBS.

SEAP expression levels from all P35-expressing cell lines were higher than those from the parental Sf9 cells, and were generally comparable to SEAP levels from Tn5BI-4 cells, with the exception of measurements at 2-3 days post infection when SEAP levels in Tn5BI-4 cells exceeded all others (FIG. 2). SEAP accumulated to very high levels in one of the P35-expressing lines, Sf9$^{P35AcV5-1}$. SEAP levels in line Sf9$^{P35AcV5-1}$ were similar to those from Tn5B1-4 cells at 3-4 days post infection, but continued to accumulate to significantly higher levels ($\geq$2-3 fold above Sf9 cell expression) at 5-6 days post infection. By 7-9 days post infection, SEAP levels from the Sf9$^{P35AcV5-1}$ line exceeded that from parental Sf9 cells by approximately 4 fold and were approximately 2 fold more than SEAP levels from Tn5B1-4 cells. High level protein production in Sf9$^{P35AcV5-1}$ cells appears to result from a prolonged infection cycle compared with the infection cycle of AcMNPV infected Sf9 cells. In typical baculovirus expression vector infection of Sf9 or Tn5B1-4 cells, foreign protein accumulation plateaus after approximately 120 hours post infection. In contrast, secreted proteins continued to accumulate until 216 hours post infection in both Sf9$^{P35AcV5-1}$ and Sf9$^{P35AcV5-3}$ cells B-Galactosidase Expression in Serum-Containing Media Sf9 or stably transfected cells expressing P35 were plated at 3×10$^5$ cells/well and Tn5B1-4 cells were plated at 1×10$^5$ cells/well in 24 well plates to measure levels of B-galactosidase. Cells were infected with virus AcMNPV-246 (which contains an *E. coli* lacZ gene and expresses the B-galactosidase reporter protein) at an MOI of 10 as described above. Cells were collected at 2, 3, 4, 5, 6, 7, 8, or 9 days post infection for production of lysates (FIG. 3). Analysis of B-galactosidase activity was performed essentially by a technique being known in the art, and herein incorporated by reference (Wang, P., Granados, R. R. and Shuler, M. L., 1992). Lysates from each sample were prepared by placing cells in 100 µl PBS, then freezing and thawing the cells three times (10 min at −70° C., 10 min at 37° C.) followed by centrifugation for 5 minutes at 12,000×g to remove debris. Supernatants were decanted and 20 µl was used for each B-galactosidase reaction.

Each B-galactosidase reaction was incubated at 28° C. and B-galactosidase activity was monitored by readings at OD420 nm and compared to a standard curve. International units (IU) of B-galactosidase activity were calculated as described earlier (Yu, Z., Podgwaite, J. D. and Wood, H. A., 1992). For each time point in FIG. 3, three infections were performed. Data collected at each time point represents B-galactosidase accumulation from initiation of infection through the indicated time. Because the cell types compared in this study differ in size and volume, expression levels of B-galactosidase were calculated as 1) international units (IU)/cell and 2) IU/mg cell protein.

Cell lines expressing AcMNPV P35 or tagged P35 were compared with Sf9 and Tn5B1-4 cell lines. Generally, in infected P35-expressing cell lines, B-galactosidase levels were slightly higher than those observed in the infected control Sf9 cells (FIG. 3). One stably transfected P35 line, $Sf9^{P35AcV5-1}$, exhibited B-galactosidase expression levels that consistently exceeded those from Sf9 cells, with increased expression in this case ranging from approximately 2.3-2.7 fold from 4-8 days post infection. Thus, one P35-expressing cell line was superior to Sf9 cells for expression of B-galactosidase. However, expression from line $Sf9^{P35AcV5-1}$ did not exceed that in Tn5B1-4 cells under these conditions, as B-galactosidase expression in Tn5B1-4 cells was consistently higher than both Sf9 and the best stably transfected P35-expressing line (FIG. 3, Tn5B1-4 vs. $Sf9^{P35AcV5-1}$).

SEAP Expression in Serum-Free Media

Serum-free media formulations are routinely used for cell propagation and protein production from recombinant baculoviruses. For comparisons of Sf9 and P35 expressing cells in serum-free medium, Sf9, Tn5B1-4, and stably transfected P35 lines $Sf9^{P35AcV5-1}$ and $Sf9^{P35AcV5-3}$ were initially grown in TNMFH medium supplemented with 10% fetal bovine serum. These cells were subsequently adapted to serum-free medium (Sf900-II; Life Technologies, Inc., Rockville, Md.). After adaptation to serum-free medium, these cells were passaged approximately eight times. Then, cells were infected with virus rAcMNPV-SEAP and SEAP assays performed on cell culture supernatants as described above. Supernatants were collected at 2, 3, 4, 5, 6, 7, 8 and 9 days post infection and SEAP levels determined.

Figure 4:
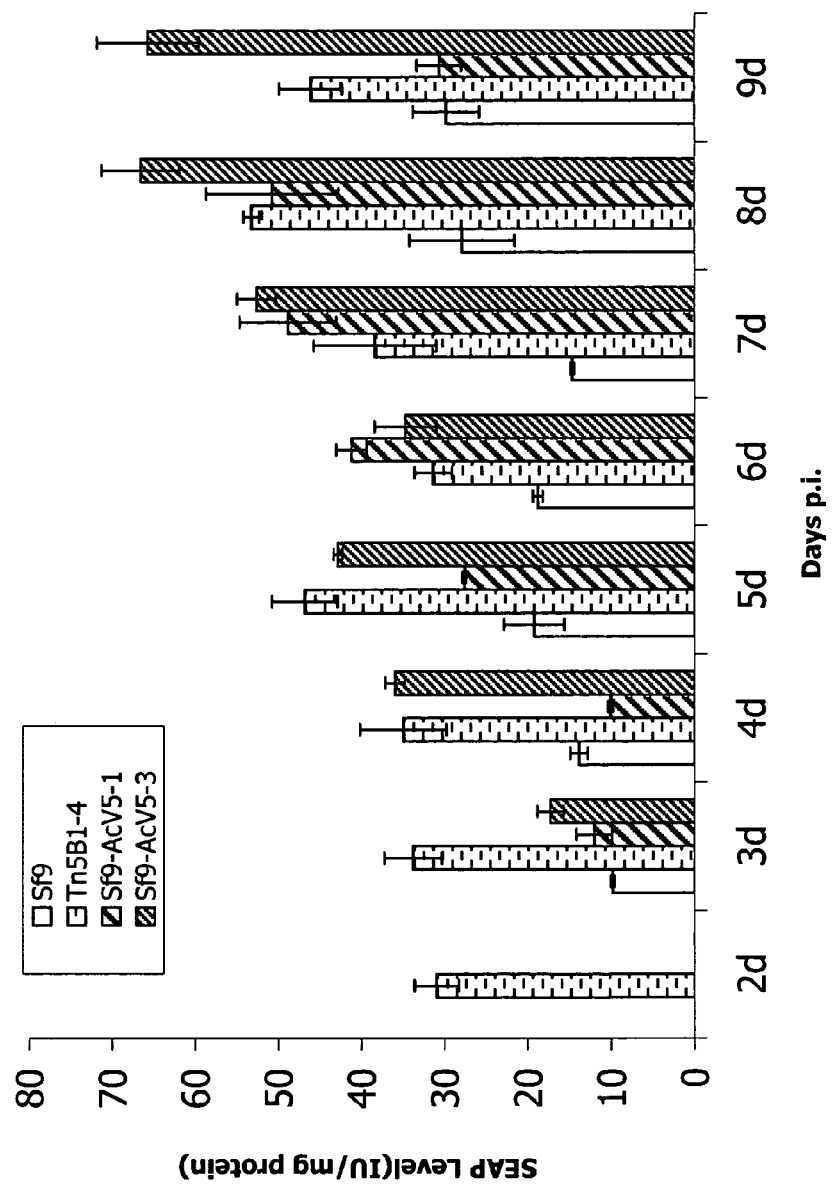
FIG. 4 shows secreted alkaline phosphatase (SEAP) levels from the supernatants of cell lines infected with virus rAcMNPV-SEAP and grown in serum-free medium (Sf900-II).

When SEAP activity in serum free medium was examined, it was observed that, from 3-9 days post infection, accumulated SEAP levels in Tn5BI-4 cells were significantly higher (1.54-2.6 fold) than in Sf9 cells (FIG. 4). Also, from 5-9 days post infection, SEAP expression from stably transfected P35-expressing cells was significantly higher (1.7-2.2 fold) than in Sf9 cells (FIG. 4). Generally, SEAP expression levels from stably transfected P35 cells was similar to that from Tn5B1-4 cells, although one cell line ($Sf9^{P35AcV5-3}$) appeared to have slightly higher levels than that from Tn5BI-4 cells from 7-9 days post infection.

Western Blot Analysis

Increasing numbers of cells ($0.5 \times 10^6$, $1 \times 10^6$, and $2 \times 10^6$ cells) from each cell line were examined on Western blots and relative P35 levels were quantified by fluorescence imaging. $Sf9^{P35AcV5-1}$ and $Sf9^{P35AcV5-3}$ cells were collected and washed twice with PBS. Proteins were denatured by heating to 100° C. for 5 minutes in Laemmli buffer and electrophoresed on a sodium dodecyl sulfate polyacrylamide gel electrophoresis (SDS-PAGE) gel. Proteins were transferred to Immobilon-P membrane (Millipore Corp., Bedford, Mass.) and the epitope-tagged P35 protein was detected using monoclonal antibody AcV5 (1:500 dilution) as a primary antibody, and a goat anti-Mouse IgG alkaline phosphatase conjugate as a secondary antibody (1:10,000 dilution). For semi-quantitative comparisons, an ECF substrate, Diethanolamine (Amersham Pharmacia Biotech, Piscataway, N.J.), was used for protein immunodetection on a Storm laser scanning system (Molecular Dynamics, Inc.).

Figure 5:
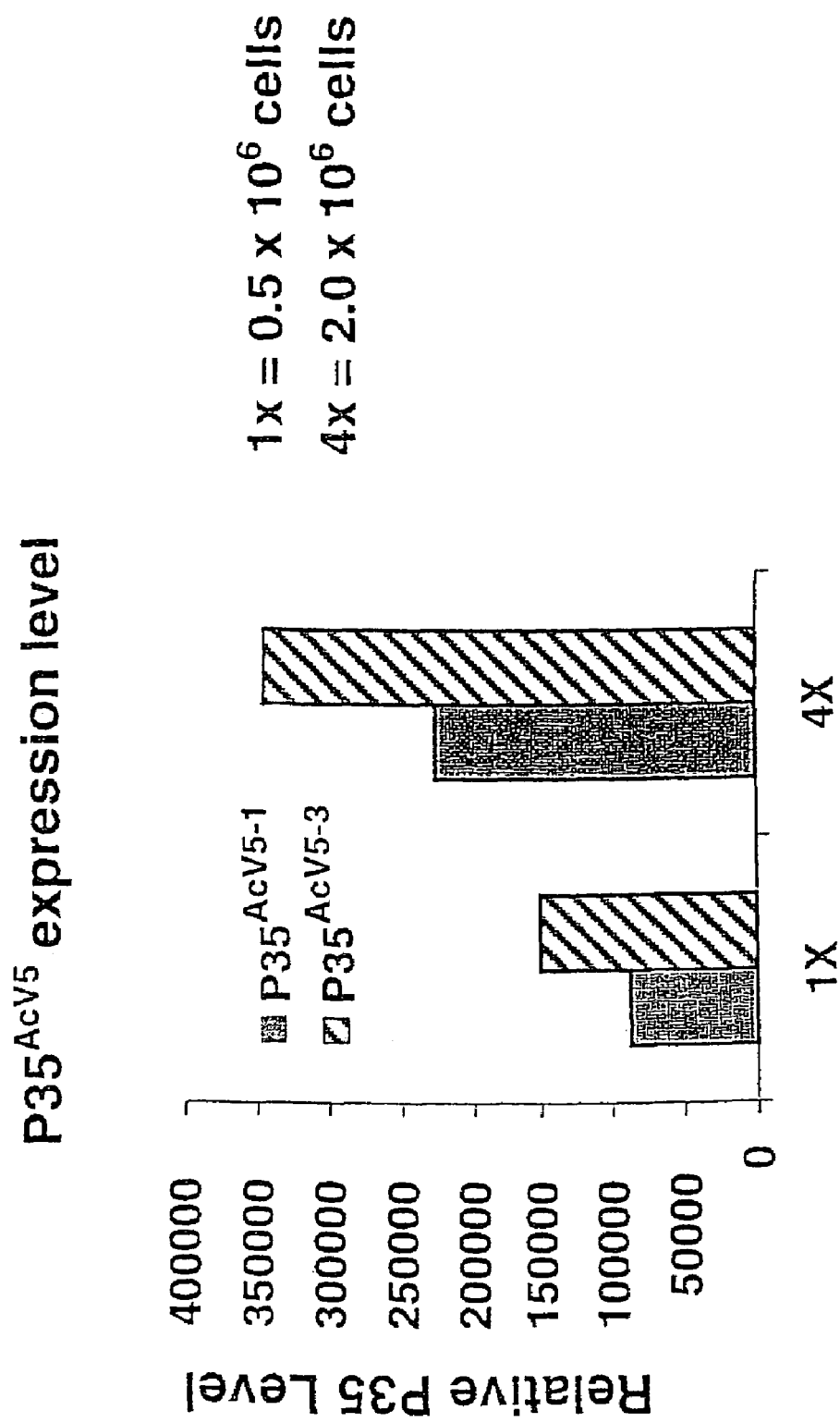
FIG. 5 shows the detection and relative expression levels of P35 as established by Western blot analysis of $Sf9^{P35AcV5-1}$ and $Sf9^{P35AcV5-3}$ cell lines.

FIG. 5 shows the relative $P35^{AcV5}$ expression levels for $P35^{AcV5-1}$ and $P35^{AcV5-3}$ cells. The 1× column shows the relative expression levels from $0.5 \times 10^6$ cells, while the 4× column shows the relative expression levels from $2.0 \times 10^6$ cells. P35 fusion proteins were identified by incubation with MAb AcV5 and proteins were quantified by enhanced chemifluorescence.

From these comparisons, it was estimated that the AcV5-tagged P35 protein from line $Sf9^{P35AcV5-3}$ was present at levels approximately 1.5-1.7× above that detected from line $Sf9^{P35AcV5-1}$. Thus, the levels of P35 detected in the two cell lines do not differ substantially.

Gene Copy Number

Southern blot hybridization analysis was used to determine p35 gene copy number in stably transfected cell lines. A PCR amplified 908 bp DNA fragment containing the AcMNPV p35 gene open reading frame was labeled with either digoxigenin (DIG) using random primers (DIG High Prime Labeling and Detection Starter Kit 1, Boehringer Mannheim company) or with $^{32}$P-dATP (DECAprime 11 Random Priming Kit, Ambion, Inc., Austin, Tex.), and used as a probe for high stringency hybridization analysis. For Southern blots, 20 μg DNA from each cell line ($Sf9^{P35AcV5-1}$ or $Sf9^{P35AcV5-3}$) was digested with EcoRI and XbaI, and electrophoresed and blotted onto positive charged nylon membrane (Micron Separations Inc.).

Either 0.1, 0.3, 0.5, 0.7 or 1.0 μg p166-p35-AcV5 plasmid DNA (digested with EcoRI and XbaI) was mixed with 20 μg Sf9 cell DNA (also digested with EcoRI and XbaI), electrophoresed and blotted to generate a standard curve for quantitative analysis. Increasing quantities of plasmid DNAs in each lane simulated increasing copy numbers of the p35 gene in the Sf9 genome. Hybridization data from these experiments was used to generate a standard curve for gene copy number. Two separate experiments were performed to compare a standard curve of p35 DNA to p35 DNA detected in lines $Sf9^{P35AcV5-1}$ and $Sf9^{P35\ AcV5-3}$.

The haploid Sf9 cell genome was estimated as approximately $5 \times 10^8$ base pairs, based on the approximated size of the Bombyx mori genome (Rasch, E. M., 1974, Gage, L. P., 1974). Estimates for gene copy number per haploid genome in $Sf9^{P35AcV5-1}$ and $Sf9^{P35AcV5-3}$ were derived from comparisons of hybridization signal strength between these cell lines and the standard curve reconstructed from plasmid DNA. Data were adjusted to the estimated size of the Sf9 genome. The data suggested that line $Sf9^{P35AcV5-1}$ contains approximately 12 copies of the p35 gene per haploid genome, while line $Sf9^{P35AcV5-3}$ contains approximately 2 copies of the p35 gene per haploid genome. Protein expression levels for these two cell lines do not correlate well with the relative number of copies of p35 in the genome. A possible explanation for this fact is that expression levels may be more dramatically affected by the site of integration rather than by the number of integration events.

Resistance of the Cell Lines to Actinomycin D and Nutrient Stress

The cells were examined for resistance to induction of apoptosis by actinomycin D, as well as survival under conditions of nutrient deprivation. Sf9 cells or stably transfected lines $Sf9^{P35AcV5-1}$ and $Sf9^{P35AcV5-3}$ were incubated in medium containing 0.1 μg/ml actinomycin D for 1 hour, then placed in TNMFH medium. After three days, all Sf9 cells died, while both $Sf9^{P35AcV5-1}$ and $Sf9^{P35AcV5-3}$ cells survived. Thus, both P35-expressing cell lines exhibited resistance to actinomycin D.

Increasing doses of actinomycin D were tested to further examine the degree of resistance to this inducer of apoptosis. Sf9 or stably transfected cells expressing P35 were incubated in a range of concentrations of actinomycin D (0.01 to 0.5

μg/ml) for one hour, then placed in TNMFH and scored for cell survival after 1-4 days (Table 2).

Apoptosis was induced in wild type Sf9 cells at actinomycin D concentrations between 0.05 μg/ml and 0.1 μg/ml (and higher) (Table 2A), whereas both P35-expressing cell lines (Sf9$^{P35AcV5}$ and Sf9$^{P35AcV5-3}$) were sensitive to actinomycin D only at higher concentrations between 0.25 μg/ml and 0.5 μg/ml (Table 2B and 2C). Resistance to actinomycin D as an inducer of apoptosis appears to be ≧2 fold, since survival of Sf9 cells was high (approximately 80-95%) at 0.075 μg/ml actinomycin D and was reduced to ≦5% at 0.1 μg/ml (Table 2A). In contrast, survival of both stably transfected lines was 100% at 0.25 μg/ml actinomycin D, and both were reduced to ≦10% at 0.5 μg/ml (Table 2B and 2C).

TABLE 2

Resistance to Induction of Apoptosis

| μg/ml Actinomycin D | 0.01 | 0.025 | 0.05 | 0.075 | 0.1 | 0.25 | 0.5 |
|---|---|---|---|---|---|---|---|
| (A) Sf9 Cell Survival (Percentage) | | | | | | | |
| Day 1 | 100 | 100 | 100 | 95 | 13.7 | 4.5 | 0 |
| Day 2 | 100 | 100 | 100 | 90 | 8.6 | 3.6 | 0 |
| Day 3 | 100 | 100 | 100 | 83 | 3.7 | 0 | 0 |
| Day 4 | 100 | 100 | 100 | 83 | 0 | 0 | 0 |
| (B) Sf9P35AcV5-1 Cell Survival (Percentage) | | | | | | | |
| Day 1 | 100 | 100 | 100 | 100 | 100 | 100 | 8.5 |
| Day 2 | 100 | 100 | 100 | 100 | 100 | 100 | 5.7 |
| Day 3 | 100 | 100 | 100 | 100 | 100 | 100 | 1.5 |
| Day 4 | 100 | 100 | 100 | 100 | 100 | 100 | 0 |
| (C) Sf9P35AcV5-3 Cell Survival (Percentage) | | | | | | | |
| Day 1 | 100 | 100 | 100 | 100 | 100 | 100 | 9.2 |
| Day 2 | 100 | 100 | 100 | 100 | 100 | 100 | 8.5 |
| Day 3 | 100 | 100 | 100 | 100 | 100 | 100 | 1.5 |
| Day 4 | 100 | 100 | 100 | 100 | 100 | 100 | 0 |

To further examine resistance to apoptosis by P35 expressing cells, Sf9, Sf9$^{P35AcV5-1}$ and Sf9$^{P35AcV5-3}$ cells were plated at 2×10$^6$ cells/well in 6-well plates, then exposed to actinomycin D (0.1 μg/ml) for one hour, and incubated in fresh TNMFH medium at 27° C. for 24 hours. Cells were harvested and washed twice with PBS. Lysates were prepared by incubating cells in 200 μl lysis buffer (10 mM Tris pH 7.5, 25 mM EDTA, 0.2% Triton X-100) for one hour at room temperature. The lysate was extracted once with phenol, once with phenol:chloroform (1:1), twice with chloroform, and then precipitated in two volumes of ethanol. Cellular DNA was resuspended in 30 μl water containing RNAse A (50 μg/ml). 10 μl of DNA from each cell treatment was electrophoresed on a 1.2% agarose gel in TBE buffer (not shown).

Examination of the DNA on ethidium bromide stained gels indicated that treatment of Sf9 cells with actinomycin D resulted in a DNA laddering effect typical of apoptosis. Degradation of the DNA into DNA ladders (compared to an untreated control) was apparent in the electrophoresed DNA from Sf9 cells. In contrast, the treated DNA extracted from both Sf9$^{P35AcV5-1}$ and Sf9$^{P35AcV5-3}$ cells showed little or no laddering or degradation. Thus, induction of apoptosis was not observed in Sf9$^{P35AcV5-1}$ and Sf9$^{P35AcV5-3}$ cells after exposure to 0.1 μg/ml actinomycin D. These results are consistent with the cell survival studies shown in Table 2.

Figure 6:
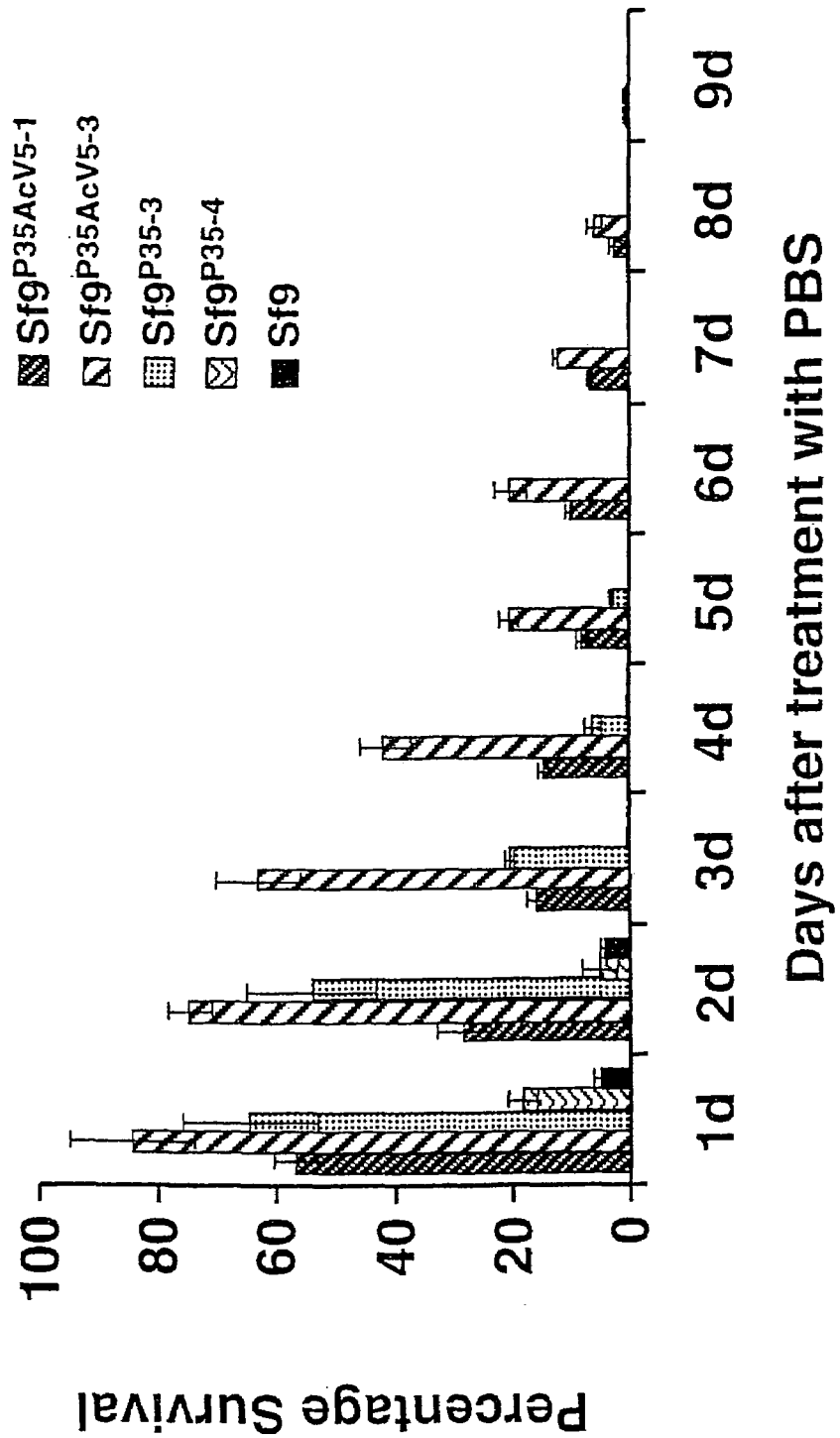
FIG. 6 shows an analysis of viability of various cell lines under conditions of nutrient stress.

Since lines Sf9$^{P35AcV5-1}$ and Sf9$^{P35AcV5-3}$ were resistant to induction of apoptosis, these lines were also examined for resistance to nutrient stress by culturing cells in phosphate buffered saline (with no nutrients added) for extended periods. Sf9, Sf9$^{P35AcV5-1}$ and Sf9$^{P35AcV5-3}$ cells were plated in TNMFH medium. After a 2-hour attachment and equilibration period, TNMFH medium was removed and replaced with PBS (pH 7.1) and incubated at 27° C. for 9 days. Cells were scored for viability at 24 hours intervals. The percentage of cells surviving at daily intervals and a comparison of cell survival are shown in FIG. 6. For example, when cells were examined at 20 hours post infection, Sf9$^{P35AcV5-3}$ cells were rounded with a large nucleus, dense cytoplasm, and little or no granularity of the cells. Essentially, these cells appeared healthy and intact. In contrast, Sf9 cells similarly incubated in PBS and examined at 20 hours post infection were mostly granular and shriveled in appearance, indicative of extensive cell lysis.

After 24 hours in PBS, viability of Sf9$^{P35AcV5-1}$ and Sf9$^{P35AcV5-3}$ cells was approximately 85% and 55% respectively. In contrast, viability of Sf9 cells was less than 5% at the same time point. Line Sf9$^{P35AcV5-3}$ exhibited the greatest degree of resistance to nutrient stress as viability of Sf9$^{P35AcV5-3}$ cells remained above 40% after 4 days in PBS. Lines Sf9$^{P35AcV5-1}$ and Sf9$^{P35-3}$ also showed much greater resistance to nutrient stress than Sf9 cells, but in these lines cell viability dropped from ≧55% at 1 day, to around 15-20% after 3 days in PBS. No surviving Sf9 cells were observed after 4 days in PBS. Notably, some cells stably expressing P35 (Sf9$^{P35AcV5-1}$ and Sf9$^{P35AcV5-3}$) remained viable through 7-8 days in PBS. Thus, the stably transfected cell lines show an extraordinary resistance to nutrient deprivation when compared with unmodified Sf9 cells.

To examine the potential long-term effects of nutrient deprivation on Sf9$^{P35AcV5-1}$ and Sf9$^{P35AcV5-3}$ cells, these cells were placed in PBS buffer for 5 days as described above, then returned to TNMFH medium. In both cases, cells recovered and grew normally. When infected with the rAcMNPV-SEAP virus, expression levels of SEAP in the supernatant were similar to those from the same cell lines which had not been exposed to nutrient stress (not shown). Thus, exposure to extreme nutrient stress did not appear to affect the capacity of these cells to express recombinant proteins at high levels.

CONCLUSIONS

Foreign gene expression in insect cells has proven to be a tool of major importance in research, as well as industrial scale production of recombinant proteins. Sf9 cells are well suited for large scale culture applications, as they are known to express reasonably high levels of recombinant proteins and they adapt readily both to suspension culture and serum-free media preparations. However, Sf9 cells are somewhat fastidious, since they do not readily tolerate nutrient stress or high-density growth.

The invention demonstrates that by stably expressing a viral suppressor of apoptosis, such as the baculovirus P35 protein, in an insect cell line, such as Sf9, novel cell lines are generated and these cells are resistant to the induction of apoptosis, resistant to nutrient stress, and support substantially higher levels of protein expression than the parental cell line. The stable transfection of viral genes capable of suppressing apoptosis into a pre-existing cell line creates more hardy cells. The novel cell lines overcome the disadvantages of their parental cell line, Sf9. These cells express levels of recombinant proteins (secreted) at levels higher than that from the parental cell line (Sf9) and comparable to the most highly productive cell line available (Tn5B1-4). It is not entirely clear how expression of P35 from the cell line results in these phenomena, since P35 is normally expressed from AcMNPV early in infection. It is possible that the accumulation of P35 in the cell prior to infection permits the infection to persist in the cells for longer periods or facilitates the maintenance of a more healthy cellular physiological state throughout infection. The presence of P35 in the cell before infection provides substantial benefits, including the expression of foreign genes.

Characterized cell lines derived from Sf9 cells and expressing the AcMNPV p35 gene are easily adapted to serum-free medium and grow readily in suspension cultures. Engineered suppressor of apoptosis genes, such as the AcMNPV p35 gene, as well as plasmids containing the suppressor of apoptosis gene(s) and antibiotic resistance genes, are useful for engineering other cell lines.

As an example, viral SA proteins could be engineered for expression in mammalian cells such as COS cells or NIH3T3 cells, for improved culture characteristics. The incorporation of viral SA proteins may affect production of valuable proteins in these cells or make them susceptible to additional pathogens. The replication of certain viruses in certain mammalian cell lines may be limited by the induction of apoptosis, which prevents productive infection and virus replication. By incorporating viral SA proteins into these cells, they may become useful for new applications, including protein expression in mammalian cells or the propagation or study of other viruses (for example, retroviral vectors).

The use of suppressors of apoptosis such as P35 improves cell lines for protein expression with baculovirus expression vectors. The P35-expressing cells have good market potential for industrial and/or pharmaceutical applications in which scaleup production of insect cells (prior to infection) is necessary, and high-level protein production is essential. In addition, Sf9 or other cell lines can be engineered with P35 or other suppressors of apoptosis. The technology is easy to apply to existing expression systems. It requires only the use of a different cell line for expression of foreign proteins. The invention permits increased flexibility in handling and scale-up of cell lines for many applications.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

REFERENCES

The following references are cited in the application and hereby incorporated by reference in their entirety.

Ayres, M. D., Howard, S. C., Kuzio, J., Lopez-Ferber, M. and Possee, R. D. The complete DNA sequence of *Autographa californica* nuclear polyhedrosis virus. *Virology* 202 (2), 586-605 (1994)

Beidler, D. R., Tewari, M., Friesen, P. D., Poirier, G. and Dixit, V. M. The Baculovirus p35 protein inhibits Fas- and tumor necrosis factor-induced apoptosis. *J Biol Chem* 270, 16526-16528 (1995).

Bertin, J. et al. Apoptotic suppression by baculovirus P35 involves cleavage by and inhibition of a virus-induced CED-3-ICE-like protease. *Journal of Virology.* 70, 6251-6259 (1996).

Blissard, G. W. and Rohrmann, G. F. Baculovirus gp64 gene expression: Analysis of sequences modulating early transcription and transactivation by IE1. *J. Virol.* 65, 5820-5827 (1991).

Bump, N. J. et al. Inhibition of ICE family proteases by baculovirus antiapoptotic protein p35. *Science* 269, 1885-1888 (1995).

Cartier, J. L., Hershberger, P. A. and Friesen, P. D. Suppression of apoptosis in insect cells stably transfected with baculovirus p35: Dominant interference by N terminal sequences p35 (1-76). *J Virology* 68, 7728-7737 (1994).

Chang, M. J., Kuzio, J. and Blissard, G. W. Modulation of translational efficiency by contextual nucleotides flanking a baculovirus initiator AUG codon. *Virology* 259, 369-383 (1999).

Clem, R. J., Fechheimer, M. and Miller, L. K. Prevention of apoptosis by a baculovirus gene during infection of insect cells. *Science* 254, 1388-1390 (1991).

Cryns, V. and Yuan, J. Proteases to die for [published erratum appears in Genes Dev 1999 Feb. 1, 13(3): 371]. *Genes Dev* 12, 1551-1570 (1998).

Davis, T. R. et al. Comparative recombinant protein production in eight insect cell lines. *In Vitro Cell Dev Biol* 29A, 388-390 (1993).

Davis, T. R., Trotter, K. M., Granados, R. R. and Wood, H. A. Baculovirus expression of alkaline phosphatase as a reporter gene for evaluation of production, glycosylation and secretion. *Biotechnology* (NY) 10, 1148-1150 (1992).

Fisher, A. J., Cruz, W., Zoog, S. J., Schneider, C. L. and Friesen, P. D. Crystal structure of baculovirus P35: role of a novel reactive site loop in apoptotic caspase inhibition. *Embo J* 18, 2031-2039 (1999).

Gage, L. P. The *Bombyx mori* genome: analysis by DNA reassociation kinetics. *Chromosoma* 45, 27-42 (1974).

Granados, R. R. and Hashimoto, Yoshifumi, Chapter 1: Infectivity of Baculoviruses to Cultured Cells, pp. 3-13. in *Invertebrate Cell System Applications, Volume II*, Jun Mitsuhashi, Editor, CRC Press, Florida, 1989.

Hay, B. A., Wolff, T. and Rubin, G. M. Expression of baculovirus P35 prevents cell death in *Drosophila. Development* 120, 2121-2129 (1994).

Hershberger, P. A., Lacount, D. J. and Friesen, P. D. The apoptotic suppressor P35 is required early during baculovirus replication and is targeted to the cytosol of infected cells. *Journal of Virology* 68, 3467-3477 (1994).

Martin, S. J. and Green, D. R. Protease activation during apoptosis: death by a thousand cuts? *Cell* 82, 349-352 (1995).

Martinou, I. et al. Viral Proteins E1B 19K and p35 Protect Sympathetic Neurons from Cell Death Induced by NGF Deprivation. *Journal of Cell Biology.* 128, 201-208 (1995).

Milner, A. E., Johnson, G. D., and Gregory, C. D. Prevention of Programmed Cell Death in Burkitt Lymphoma Cell Lines by bc1-2 Dependent and Independent Mechanisms. *International Journal of Cancer* 52: 636-644 (1992).

Monsma, S. A. and Blissard, G. W. Identification of a membrane fusion domain and an oligomerization domain in the baculovirus GP64 Envelope Fusion Protein. *J. Virol.* 69, 2583-2595 (1995).

Monsma, S. A., Oomens, A. G. P. and Blissard, G. W. The GP64 Envelope Fusion Protein is an essential baculovirus protein required for cell to cell transmission of infection. *J. Virol.* 70, 4607-4616 (1996).

Rabizadeh, S., Lacount, D. J., Friesen, P. D., and Bredesen, D. E. Expression of the baculovirus p35 gene inhibits mammalian neural cell death. *Journal of Neurochemistry* 61, 2318-2321 (1993).

Rasch, E. M. The DNA content of sperm and hemocyte nuclei of the silkworm, *Bombyx mori L. Chromosoma* 45, 1-26 (1974).

Robertson, N. M. et al. Baculovirus P35 inhibits the glucocorticoid-mediated pathway to cell death. *Cancer Research.* 57, 43-47 (1997).

Singh, R. P., Emery, A. N., and Al-Rubeai, M. Enhancement of Survivability of Mammalian Cells by Overexpression of the Apoptosis-Suppressor Gene bc1-2. *Biotechnology and Bioengineering* 52, 166-175 (1996).

Sugimoto, A., Friesen, P. D. and Rothman, J. H. Baculovirus p35 prevents developmentally programmed cell death and rescues a ced-9 mutant in the nematode *Caenorhabditis elegans*. *EMBO J.* 13, 2023-2028 (1994).

Wang, P., Granados, R. R. and Shuler, M. L. Studies on serum-free culture of insect cells for virus propagation and recombinant protein production. *J Invertebr Pathol* 59, 46-53 (1992).

Wickham, T. J., Davis, T., Granados, R. R., Shuler, M. L. and Wood, H. A. Screening of insect cell lines for the production of recombinant proteins and infectious virus in the baculovirus expression system. *Biotechnol Prog* 8, 391-396 (1992).

Xue, D. and Horvitz, H. R. Inhibition of the *Caenorhabditis elegans* cell-death protease CED-3 by a CED-3 cleavage site in baculovirus p35 protein. *Nature (London)* 377, 248-251 (1995).

Yu, Z., Podgwaite, J. D. and Wood, H. A. Genetic engineering of a *Lymantria dispar* nuclear polyhedrosis virus for expression of foreign genes. *J Gen Virol* 73, 1509-1514 (1992).

What is claimed is:

1. A composition comprising a baculovirus expression system for expressing a recombinant protein, including:
   a) a baculovirus that has a functional p35 gene, and is engineered to express a recombinant protein;
   b) a cultured Sf9 cell line that is susceptible to infection by said baculovirus, and is engineered by transfection with a first recombinant expression vector to express a recombinant polynucleotide that encodes AcNPV p35, wherein said recombinant polynucleotide is cloned into said first recombinant expression vector such that said recombinant polynucleotide is capable of being expressed in said cell line;
   c) said first recombinant expression vector being delivered into at least one cell of said cultured cell line; and
   d) said at least one cell being infected by said baculovirus;
   e) such that apoptosis is inhibited, when said engineered cell line is infected by said baculovirus that includes a functional p35 gene.

2. The composition of claim 1, further comprising a second recombinant DNA expression vector including a recombinant DNA that encodes a selectable marker.

3. A method for expressing a recombinant protein in a baculovirus expression system, comprising the steps of:
   a) engineering a baculovirus that has a functional p35 gene to express a recombinant protein;
   b) culturing an Sf9 cell line that is susceptible to infection by said baculovirus, and is engineered by transfection with a first recombinant expression vector to express a recombinant polynucleotide that encodes AcNPV p35, wherein said recombinant polynucleotide is cloned into said first recombinant expression vector such that said recombinant polynucleotide is capable of being expressed in said cell line;
   c) delivering said first recombinant expression vector into at least one cell of said cultured cell line; and
   d) infecting said at least one cell with said baculovirus, such that apoptosis is inhibited, when said engineered cell line is infected by said baculovirus that includes a functional p35 gene.

4. The method of claim 3, further comprising the step of engineering said cell line by transformation with a second recombinant expression vector to express a recombinant polynucleotide that encodes a selectable marker.

5. A method of developing a cell line containing a suppressor of apoptosis, comprising the steps of:
   a) isolating a recombinant polynucleotide that encodes AcNPV p35;
   b) constructing a first recombinant expression vector wherein said recombinant polynucleotide is cloned into said first recombinant expression vector such that said recombinant polynucleotide is capable of being expressed in said cell line;
   c) delivering said first recombinant expression vector into at least one Sf9 cell;
   d) exposing said at least one cell to any inducer of apoptosis; and
   e) selecting said cell lines from said at least one cell which survives exposure to said inducer of apoptosis, such that apoptosis induced by a subsequent baculovirus infection is inhibited, when said baculovirus includes a functional p35 gene.

6. A cultured cell line comprising an Sf9 insect cell line that is susceptible to infection by a baculovirus, and is engineered to stably express a recombinant polynucleotide that encodes AcNPV p35.

7. A cell line selected from the group consisting of ATCC accession number PTA-3099 and ATCC accession number PTA-3100.

* * * * *